(12) United States Patent
Takahara et al.

(10) Patent No.: US 9,046,479 B2
(45) Date of Patent: Jun. 2, 2015

(54) BIOSENSOR, METHOD OF PRODUCING THE SAME AND DETECTION SYSTEM COMPRISING THE SAME

(75) Inventors: Yoshifumi Takahara, Ehime (JP); Noriyoshi Terashima, Ehime (JP); Takaaki Fujii, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 806 days.

(21) Appl. No.: 12/490,699

(22) Filed: Jun. 24, 2009

(65) Prior Publication Data

US 2009/0321257 A1    Dec. 31, 2009

(30) Foreign Application Priority Data

Jun. 24, 2008    (JP) ................. 2008-164562

(51) Int. Cl.
*G01N 27/327*    (2006.01)

(52) U.S. Cl.
CPC ......... *G01N 27/3272* (2013.01); *Y10T 29/4913* (2015.01)

(58) Field of Classification Search
USPC ............. 204/403.01–403.15; 205/777.5, 792, 205/778, 775
See application file for complete search history.

(56) References Cited

U.S. PATENT DOCUMENTS

| | | |
|---|---|---|
| 2,913,386 A | 11/1959 | Clark |
| 3,539,455 A | 11/1970 | Clark |
| 3,542,662 A | 11/1970 | Hicks et al. |
| 3,770,607 A | 11/1973 | Williams |
| 3,788,950 A | 1/1974 | Hicks et al. |
| 3,838,033 A | 9/1974 | Mindt et al. |
| 3,948,745 A | 4/1976 | Guilbault et al. |
| 3,979,274 A | 9/1976 | Newman et al. |
| 4,073,713 A | 2/1978 | Newman et al. |
| 4,085,009 A | 4/1978 | Pace |
| 4,092,233 A | 5/1978 | Clemens et al. |
| 4,100,029 A | 7/1978 | Prosper |
| 4,224,125 A | 9/1980 | Nankai et al. |
| 4,225,410 A | 9/1980 | Pace et al. |
| 4,454,007 A | 6/1984 | Pace |
| 4,477,575 A | 10/1984 | Vogel et al. |
| 4,534,356 A | 8/1985 | Papadakis |
| 4,545,382 A | 10/1985 | Higgins et al. |

(Continued)

FOREIGN PATENT DOCUMENTS

| | | |
|---|---|---|
| EP | 0 136 362 | 4/1985 |
| JP | 4-6907 | 2/1992 |

(Continued)

OTHER PUBLICATIONS

L.C. Clark, Jr., "Monitor and control of blood and tissue oxygenation," Trans. Am. Soc. Artif. Intern. Organs, 1956 2, 41.

Voss Do., "A new oxygen electrode model for the polarographic assay of cellular and mitochondrial respiration," Anal Biochem. Sep. 6, 1963; 211-222.

(Continued)

*Primary Examiner* — J. Christopher Ball
*Assistant Examiner* — Maris R Kessel
(74) *Attorney, Agent, or Firm* — Wenderoth, Lind & Ponack, L.L.P.

(57) ABSTRACT

A biosensor detects a target substance contained in a liquid sample and includes an insulating base plate having a recess formed in a portion that is thinner than the surrounding part, a working electrode and a counter electrode, at least one of which is disposed in the recess. A reaction reagent is disposed in the recess and reacts with a specific substance in the liquid sample.

28 Claims, 22 Drawing Sheets

(56) References Cited

U.S. PATENT DOCUMENTS

| | | | |
|---|---|---|---|
| 4,711,245 A | 12/1987 | Higgins et al. | |
| 4,897,173 A | 1/1990 | Nankai et al. | |
| 4,963,245 A | 10/1990 | Weetall et al. | |
| 4,975,175 A * | 12/1990 | Karube et al. | 204/403.12 |
| 5,066,372 A | 11/1991 | Weetall et al. | |
| 5,104,480 A | 4/1992 | Wojnarowski et al. | |
| 5,120,420 A | 6/1992 | Nankai et al. | |
| 5,126,034 A | 6/1992 | Carter et al. | |
| 5,185,256 A | 2/1993 | Nankai et al. | |
| 5,229,282 A | 7/1993 | Yoshioka et al. | |
| 5,262,035 A | 11/1993 | Gregg et al. | |
| 5,264,103 A | 11/1993 | Yoshioka et al. | |
| 5,264,104 A | 11/1993 | Gregg et al. | |
| 5,264,105 A | 11/1993 | Gregg et al. | |
| 5,288,636 A | 2/1994 | Pollmann et al. | |
| 5,320,725 A | 6/1994 | Gregg et al. | |
| 5,320,732 A | 6/1994 | Nankai et al. | |
| 5,385,846 A | 1/1995 | Kuhn et al. | |
| 5,405,511 A | 4/1995 | White et al. | |
| 5,438,271 A | 8/1995 | White et al. | |
| 5,509,410 A | 4/1996 | Hill et al. | |
| 5,512,159 A | 4/1996 | Yoshioka et al. | |
| 5,512,489 A | 4/1996 | Girault et al. | |
| 5,565,085 A | 10/1996 | Ikeda et al. | |
| 5,576,073 A | 11/1996 | Kickelhain et al. | |
| 5,582,697 A | 12/1996 | Ikeda et al. | |
| 5,593,739 A | 1/1997 | Kickelhain et al. | |
| 5,593,852 A | 1/1997 | Heller et al. | |
| 5,628,890 A | 5/1997 | Carter et al. | |
| 5,650,062 A | 7/1997 | Ikeda et al. | |
| 5,665,222 A | 9/1997 | Heller et al. | |
| 5,682,884 A | 11/1997 | Hill et al. | |
| 5,708,247 A | 1/1998 | MacAleer et al. | |
| 5,727,548 A | 3/1998 | Hill et al. | |
| 5,755,953 A | 5/1998 | Henning et al. | |
| 5,758,398 A | 6/1998 | Rijnbeek et al. | |
| 5,759,364 A | 6/1998 | Charlton et al. | |
| 5,762,770 A | 6/1998 | Pritchard et al. | |
| 5,798,031 A | 8/1998 | Charlton et al. | |
| 5,820,551 A | 10/1998 | Hill et al. | |
| 5,858,691 A | 1/1999 | Hoenes et al. | |
| 5,997,817 A | 12/1999 | Crismore et al. | |
| 6,004,441 A | 12/1999 | Fujiwara et al. | |
| 6,103,033 A | 8/2000 | Say et al. | |
| 6,212,417 B1 | 4/2001 | Ikeda et al. | |
| 6,258,229 B1 | 7/2001 | Winarta et al. | |
| 6,287,451 B1 | 9/2001 | Winarta et al. | |
| 6,299,757 B1 | 10/2001 | Feldman et al. | |
| 6,309,526 B1 | 10/2001 | Fujiwara et al. | |
| 6,338,790 B1 | 1/2002 | Feldman et al. | |
| 6,416,641 B1 * | 7/2002 | Ikeda et al. | 204/403.04 |
| 6,447,657 B1 | 9/2002 | Bhullar et al. | |
| 6,461,496 B1 | 10/2002 | Feldman et al. | |
| 6,484,046 B1 | 11/2002 | Say et al. | |
| 6,540,890 B1 | 4/2003 | Bhullar et al. | |
| 6,576,101 B1 | 6/2003 | Heller et al. | |
| 6,592,745 B1 | 7/2003 | Feldman et al. | |
| 6,616,819 B1 | 9/2003 | Liamos et al. | |
| 6,618,934 B1 | 9/2003 | Feldman | |
| 6,645,359 B1 | 11/2003 | Bhullar et al. | |
| 6,755,949 B1 | 6/2004 | Bhullar et al. | |
| 6,767,440 B1 | 7/2004 | Bhullar et al. | |
| 6,805,780 B1 * | 10/2004 | Ryu et al. | 204/403.01 |
| 6,814,843 B1 | 11/2004 | Bhullar et al. | |
| 6,814,844 B2 | 11/2004 | Bhullar et al. | |
| 6,830,669 B2 * | 12/2004 | Miyazaki et al. | 204/409 |
| 6,866,758 B2 | 3/2005 | Bhullar et al. | |
| 6,911,621 B2 | 6/2005 | Bhullar et al. | |
| 7,003,340 B2 | 2/2006 | Say et al. | |
| 7,073,246 B2 | 7/2006 | Bhullar et al. | |
| 7,312,042 B1 | 12/2007 | Petyt et al. | |
| 7,390,391 B2 | 6/2008 | Nagakawa et al. | |
| 7,771,926 B2 | 8/2010 | Petyt et al. | |
| 8,012,322 B2 * | 9/2011 | Park et al. | 204/403.04 |
| 8,211,632 B2 | 7/2012 | Petyt et al. | |
| 2003/0146113 A1 * | 8/2003 | Unkrig et al. | 205/792 |
| 2004/0108206 A1 | 6/2004 | Bhullar et al. | |
| 2004/0245121 A1 | 12/2004 | Nagakawa et al. | |
| 2005/0067277 A1 | 3/2005 | Pierce et al. | |
| 2005/0205422 A1 * | 9/2005 | Moser et al. | 204/403.06 |
| 2006/0175199 A1 | 8/2006 | Huang | |
| 2007/0095661 A1 | 5/2007 | Wang et al. | |
| 2007/0266871 A1 | 11/2007 | Wegner et al. | |
| 2008/0101983 A1 | 5/2008 | Petyt et al. | |
| 2008/0230384 A1 | 9/2008 | Pierce et al. | |
| 2009/0000947 A1 * | 1/2009 | Akahori et al. | 204/403.14 |
| 2009/0071847 A1 | 3/2009 | Edelbrock et al. | |
| 2010/0084268 A1 | 4/2010 | Pierce et al. | |
| 2010/0276303 A1 | 11/2010 | Fujiwara et al. | |
| 2011/0031110 A1 | 2/2011 | Wang et al. | |
| 2011/0099786 A1 | 5/2011 | Petyt et al. | |
| 2013/0031772 A1 | 2/2013 | Petyt et al. | |

FOREIGN PATENT DOCUMENTS

| | | |
|---|---|---|
| JP | 2000-097899 | 4/2000 |
| JP | 2002-541453 | 12/2002 |
| JP | 2003-207475 | 7/2003 |
| JP | 2004-226358 | 8/2004 |
| JP | 2004226358 A * | 8/2004 |
| JP | 2004-325184 | 11/2004 |
| JP | 2005-249530 | 9/2005 |
| JP | 2007-507711 | 3/2007 |
| JP | 2007-330510 | 12/2007 |
| JP | 2009-536734 | 10/2009 |
| JP | 2009-537825 | 10/2009 |
| JP | 2010-507805 | 3/2010 |
| WO | 03/025558 | 3/2003 |
| WO | WO 2006132250 A1 * | 12/2006 |
| WO | 2007/053497 | 5/2007 |
| WO | WO 2007078315 A2 * | 7/2007 |
| WO | 2007/133457 | 11/2007 |
| WO | 2007/136980 | 11/2007 |
| WO | 2008/047842 | 4/2008 |
| WO | 2008/051407 | 5/2008 |

OTHER PUBLICATIONS

Updike, SJ. et al., "The enzyme electrode," Nature Jun. 3, 1967; 214(5092): 986-988.
Fujihira et al., "Reversible redox titrations of cytochrome c and cytochrome c oxidase using detergent solubilized electrochemically generated mediator-titrations," Biochemical and Biophysical Research Communications 1974 61 (2): 538-543.
L.C. Thomas et al., "Voltammetric measurement of reduced Nicotinamide-Ademine Nucleotides and application to amperometric measurements of enzyme reactions," Analytica Chemica Acta 1975, 78, 271-276.
Yagi et al., "A new assay method for hydrogenase based on an enzymic electrode reaction. The enzymic electric cell method," J Biochem. Sep. 1975; 78 (3): 443-454.
Johnson, JM. et al., "Metal complex as mediator-titrants for electrochemical studies of biological systems," Anal. Biochem. Aug. 1983; 133 (1): 186-189.
Cass et al., "Ferrocene-mediated enzyme electrode for amperometric determination of glucose," Ana. Chem. Apr. 1984; 56 (4): 667-671.
D'Costa, E. J. et al., "Quinoprotein glucose dehydrogenase and its applications in an amperometric glucose sensor," Biosensors 1986 2: 71-87.
Denis, C. et al., "Effects of endurance training on hyperammonaemia during a 45-min constant exercise intensity," Eur J Appl Physiol Occup Physiol. 1989; 59 (4): 268-272.
Loughran, M. G. et al., "Amperometric detection of histamine at a quinoprotein dehydrogenase enzyme electrode," Biosensors and Bioelectronics, 1995 10: 569-576.
Loughran, M.G. et al., "Ammonium requirement and stability of methanol dehydrogenase TTF. TCNQ electrodes," The Analyst, 1996 121: 1711-1715.
Newman, JD. et al., "Home blood glucose biosensors: a commercial perspective," Biosens Bioelectron. Jun. 15, 2005; 20 (12): 2435-2453.

\* cited by examiner

BIOSENSOR, METHOD OF PRODUCING THE SAME AND DETECTION SYSTEM COMPRISING THE SAME

CROSS-REFERENCE TO RELATED APPLICATIONS

This application claims priority to Japanese Patent Application No. 2008-164562. The entire disclosure of Japanese Patent Application No. 2008-164562 is hereby incorporated herein by reference.

BACKGROUND OF THE INVENTION

1. Technical Field

The present invention relates to a biosensor used to detect or quantify a specific component in a liquid sample, and more particularly relates to a biosensor capable of accurate measurement with excellent reproducibility, and to a method of producing this biosensor, and a detection system in which this biosensor is used.

2. Description of the Prior Art

A biosensor used to measure blood glucose levels, which is a typical biosensor, can easily quantify the glucose in blood by mainly utilizing an electrochemical reaction, and is made up of two or more electrodes, a reagent that reacts with glucose, an electron transfer substance that allows the reaction to proceed smoothly, and so forth.

The technological trend in recent years with biosensors used to measure blood glucose levels is that the time it takes for measurement is being shortened to make the devices easier for patients to use, and that the amount of blood required for measurement is being reduced in order to minimize pain during puncture. In fact, the latest technology makes possible biosensors whose measurement time is only 5 seconds and in which the amount of blood measured is 0.3 µL.

Meanwhile, the rise in treatment costs that accompanies the global increase in diabetes patients in recent years has led to a greater quantity of biosensors used for measuring blood glucose levels and to a reduction in price. As a result, though, of the biosensors sold for measuring blood glucose levels, some sacrifice performance for a lower price. And measurement performance is also sometimes sacrificed for the sake of a shorter measurement time and smaller amount of blood.

Because of the above situation, there is currently a need in the marketplace for an improved and inexpensive biosensor used to measure blood glucose levels that does not sacrifice measurement performance, is easier for diabetes patients to use, and inflicts less pain.

There are known biosensors for quantifying a specific component in a liquid sample, but technical advances and terminology used by inventors vary, and can be extremely hard to understand, so the same terminology will be used, while not departing from the original meaning, to make the differences from prior art as clear as possible.

Biosensor technology has a long history, and can be traced all the way back to 1956, which Leland C. Clark suggested that an oxygen electrode capable of measuring the oxygen in a solution could be applied to a biosensor (see Patent Document 1 and Non-Patent Document 1).

Then, in 1962, Leland C. Clark described that he was able to produce an amperometric glucose oxygen electrode by using a dialysis membrane to seal a glucose oxidation enzyme in a Clark oxygen electrode (see Non-Patent Document 2).

In 1967, Updike and Hicks published an "enzyme electrode" with which a substrate in a solution could actually be measured by fixing an oxidation enzyme to an oxygen electrode surface with polyacrylamide gel, so that the oxygen was proportionally consumed in a substrate oxidation reaction within this fixing layer, and the measured current value decreased (see Patent Document 3 and Non-Patent Document 4).

The above-mentioned Clark oxygen electrode is usually a two-electrode electrolytic cell that has a platinum working electrode and a silver/silver chloride reference electrode (counter electrode). The following are the two greatest technical advances provided by a Clark oxygen electrode. 1) Because a gas permeable membrane is affixed over a platinum electrode, the measurement system and the electrode system are separate, so current response is stable and there is no admixture of substances that would hinder measurement, and 2) the oxygen consumption type of biorecognition ability of fixed oxidation enzymes, or mitochondria and other organellas, or aerobic cells (such as microbes), is utilized, and the dissolved oxygen in a liquid sample that has been reduced as a result of a substrate specific reaction is quantified, which allows a certain substrate to be measured (see, for example, Patent Documents 2, 4, 5, and 8, and Non-Patent Documents 3 and 6).

However, a drawback to a biosensor that makes use of a Clark oxygen electrode is that the measurable range is limited by the amount of oxygen dissolved in the liquid sample. In view of this, in 1975 Thomas et al. employed a coenzyme oxidized nicotinamide adenine dinucleotide (hereinafter referred to as NAD) as an electron transfer substance between an enzyme and an electrode, and reported that this was extremely effective in terms of overcoming the above-mentioned drawback to the measurable range of a Clark oxygen electrode. According to this invention, the active level of lactate dehydrogenase (hereinafter referred to as LDH) was proven to have a correlation with the result for oxidation current of a coenzyme reduced nicotinamide adenine dinucleotide (hereinafter referred to as NADH). What produces this correlation is that NADH increases in proportion to substrate concentration when a total of three electrodes are used (an auxiliary and two reference electrodes) to apply a constant voltage with a potentiostat, so the way of being converted from NADH to NAD is seen as a result of an electrochemical reaction (see Non-Patent Document 7).

Also, biosensors to which the above-mentioned invention is applied have undergone further research and development to make them more practical, such as fixing an enzyme and a coenzyme (see Patent Documents 11 and 13, for example).

Part of the above-mentioned drawback to biosensors involving the use of a Clark oxygen electrode, that the measurement range was limited, was solved by a method in which hydrogen peroxide produced in a reaction by an oxidation enzyme was amperometrically detected. This is because the amount of hydrogen peroxide increases as the enzyme reaction proceeds, unlike methods in which oxygen is measured. However, even with a method in which hydrogen peroxide is measured, a drawback is that if the liquid sample is blood, depending on the applied voltage (near +0.7 V to Ag/AgCl), various interference substances in the blood, such as ascorbic acid or uric acid, may affect the measurement result depending on their concentration.

Newman et al. introduced, as a method for eliminating the effect of the above-mentioned interference substances in amperometric detection, a method in which just hydrogen peroxide is selectively transmitted to the electrode through a cellulose membrane or the like, and just hydrogen peroxide is measured amperometrically (see Patent Documents 9 and 10).

Upon receiving these research results, the Yellow Spring Instrument company (Ohio, United States of America) in 1975 marketed a large glucose biosensor with which hydrogen peroxide was selectively transmitted with a cellulose membrane or the like, and hydrogen peroxide was measured amperometrically.

Although not currently commercially available, in 1976 the Miles company (Illinois, United States of America) marketed under the trade name of Biostator a large artificial pancreas for bedside use that employed a glucose biosensor developed by Clemens et al. (see Patent Document 12).

Thus, biosensors featuring oxygen electrodes, which were developed by Leland C. Clark and are now called first-generation biosensors, have been the subject of continuing research by fixing various oxidation enzymes. The subject of this research has been greatly expanded from just the medical field to include the environmental field and the food industry, and some of these research projects have seen commercial application, albeit in small numbers.

Even today, however, the above-mentioned industries and products have yet to achieve major commercial success. A reason for this is that, in addition to the technical problems listed up to now, first-generation biosensors are produced by glass working, which does not lend itself to mass production, and when high manufacturing costs, as well as the production of gas permeable membranes and vessels for holding electrolyte are taken into account, the sensor ends up being so large in size that it is inconvenient to use.

In view of this, in an effort to solve manufacturing problems, in 1990 Karube et al. invented a microbiosensor in which silicon was used instead of glass for the base plate, a non-liquid aqueous electrolyte-containing material was put in a groove formed by anisotropic etching, and a gas permeable membrane was added (see Patent Document 23).

However, although inventions such as the one above were intended to overcome the drawbacks to first-generation biosensors, the biosensors to which these inventions were applied have yet to reach the market. This is probably because the problems of manufacturing cost and ease of use have not been solved.

In 1992, Kawaguri et al. and Nankai et al. reported on a technique for producing a simple biosensor. They embedded a measuring electrode and a counter electrode in an insulating base plate so that the ends of the electrodes would be exposed, and disposed a porous material impregnated with enzyme to cover the exposed parts of the electrodes (see Patent Documents 89 and 26). This simplified the user's operating procedure, but biosensors in which this technology is used have yet to become popular as compact devices that allow a blood glucose level to be easily measured at home. This is probably because the problems of manufacturing cost and ease of use have not been solved.

To solve the problems associated with the first-generation biosensors discussed above, research has been conducted into next-generation biosensors in which oxygen or hydrogen peroxide is not used as an electron acceptor, and a dehydrogenase, which is a type of redox enzyme, and a reversible redox electron acceptor are combined (hereinafter referred to as second-generation biosensors) (see Non-Patent Documents 5, 8, and 9, for example).

In 1976, based on the research results of Mindt et al., the Swiss firm of Roche developed the Lactate Analyzer LA640, which makes use of second-generation biosensor technology. This apparatus uses hexacyanoferrate as a soluble electron transfer substance that facilitates the coming and going of electrons between an electrode and lactate dehydrogenase (see Patent Documents 6 and 7).

This apparatus, however, is inconvenient to use, and so was not used in medical clinical applications. Consequently, this apparatus did not enjoy commercial success (see Non-Patent Documents 11 and 14).

In 1978, Nankai et al. disclosed a method for producing an enzyme electrode by combining a redox enzyme and an electron transfer substance, and further specified a plurality of type of electron transfer substances that are useful for disposable biosensors. This indicated that potassium ferricyanide could be applied to disposable biosensors. Potassium ferricyanide is used in nearly all of the currently available biosensors used for measuring blood glucose level (see Patent Document 14).

After the invention by Nankai et al., rapid progress was made in research and development of disposable biosensors between 1980 and 2000. In 1984 ferrocene was employed as an electron transfer substance by Case et al. and Higgins et al., and it was published that a derivative thereof could be used in a practical biosensor by kneading this derivative into an electrode and fixing it (see Patent Document 20 and Non-Patent Documents 10 and 13).

The debut of the first compact amperometric biosensor for measuring blood glucose levels was achieved when the US firm of MediSense produced an enzyme electrode by screen printing (see Patent Documents 19 and 28).

However, these techniques are applications of electronic device technology, and involved the direct application of manufacturing apparatus and methods for manufacturing a printed base plate on which electronic components are mounted. In other words, they involved merely forming a plurality of wires on a non-conductive base plate, and mounting a reaction reagent, and the products were not convenient biosensors that could be used by ordinary consumers. Furthermore, prior to the inventions by Case or Higgins et al., Pace disclosed an ion-selective sensor configuration, and Papakakis disclosed a gas sensor configuration (Patent Documents 16 and 18).

Examples of the specific reasons why the biosensors of by Case or Higgins et al. were inconvenient to use are that measurement required an extremely large amount of blood, and that the measurement accuracy of the sensors was problematic because of the sensor configuration and the manufacturing method.

In view of this, Nankai et al. invented a biosensor in which electrodes were formed mainly from carbon on an insulating base plate, an insulating layer was printed over this, and the electrode surface was accurately restricted, which increased sensor accuracy, and a reaction layer, a spacer, and a cover were also disposed over the electrodes (see, for example, Patent Documents 21, 27, 29, and 371). The use of the spacer and cover dramatically reduced the amount of blood required for measurement. Ultimately, a sensor that required only 2.5 µL of blood was developed as an actual product and is marketed around the world.

This method of forming a liquid sample chamber from a spacer and cover was truly revolutionary, and is employed today in virtually all disposable biosensors used for measuring blood glucose levels. Also, the liquid sample chamber-equipped biosensor perfected by Nankai et al. led to further advances aimed at improving convenience and accuracy (see, for example, Non-Patent Document 15).

In 1993, Yoshioka et al. reported that adhesion of a reagent layer to a carbon electrode on a base plate was increased by treating the carbon electrode surface with an organic solvent. This reagent layer contained an enzyme, an electron transfer substance, and a hydrophilic polymer (see Patent Document 30). With this invention, it was discovered that a problem encountered in the mass production of disposable biosensors, namely, inconsistent quality within or between manufacturing lots, could be minimized. This served as a starting point for giving more importance to measurement accuracy even in mass-produced biosensors.

In 1993, Yoshioka et al. published a biosensor which was equipped with a main electrode system disposed on a base plate and composed of a working electrode and a counter electrode, and which further comprised a reaction layer disposed so as to be in contact with or in the vicinity of the main electrode system. This main electrode system included redox enzyme. With this biosensor, a sub-electrode system is disposed as a reference electrode so as to maintain a distance from the main electrode system. With this biosensor, it can be detected from changes in impedance detected by this reference electrode that enough of a liquid sample has been supplied to the sensor (see Patent Document 32).

With this invention, even diabetes patients who were unaccustomed to using biosensors were able to supply the electrode with the amount of blood needed for measurement with no problem. Consequently, measuring a sufficient quantity of blood should afford better performance, and it is believed that a huge reduction in measurement error should greatly decrease the burden on the patient (see, for example, Non-Patent Document 20).

Still, the following problems were encountered with this invention. A reagent hole is formed by attaching a plate having a through-hole over a base plate on which the electrodes are disposed. However, no liquid sample chamber is employed that would allow a reduction in the amount of blood needed for measurement. Accordingly, pain is inflicted on a diabetes patient, which is a problem in terms of convenience. The fact that the measurement result cannot be obtained until this reaction (the fact that the measurement can be obtained after this reaction) is complete can also be considered an inconvenience to the diabetes patient.

Also, this publication gives examples, albeit very few, of employing a reduction enzyme such as glucose dehydrogenase, rather than just a glucose oxidation enzyme, for a biosensor. An advantage of a dehydrogenase is that it is almost completely unaffected by dissolved oxygen. In particular, glucose dehydrogenase is used in many biosensors manufactured since the late 1990's, and it is also known to have great clinical significance (see, for example, Non-Patent Documents 12, 17, 18, and 19).

In 1995, Kuhn et al. disclosed a biosensor for measuring the hematocrit level of whole blood electrochemically. This biosensor was composed of a working electrode, a counter electrode, and a porous membrane that was disposed spatially separate from these electrodes and contained an electron transfer substance. When whole blood was placed on this porous membrane, a mixture of blood and the electron transfer substance formed. When this mixture reached the electrodes, a current was generated at the electrodes by applying enough potential either to oxidize or to reduce the electron transfer substance. This current was measured, and the hematocrit level was detected from the measurement result (see Patent Document 38).

This invention is a way to handle a hematocrit value, which becomes a problem as an interference substance in making blood into a liquid sample. However, if the viscosity of the blood is extremely high due to excess lipids or the like, there is some doubt as to whether this invention is an effective means. Also, with this invention, it is predicted that it will take longer from the application of a drop of blood until the measurement is complete, and furthermore a relatively large quantity of blood is necessary.

In 1995, White et al. disclosed two measurement devices, as biosensor measurement devices for measuring the amount of a target substance in a biological sample. One was a biosensor measurement device equipped with an algorithm for determining the amount of target substance according to the ambient temperature when a biological sample was in the reaction zone, and the other was a biosensor measurement device with which either a biosensor or a check strip can be inserted (see Patent Documents 39 and 40).

As shown in the above-mentioned inventions of White et al. in 1995, biosensor research and development has been aimed at improving both user convenience and measurement accuracy. This is believed to be attributable to the fact that it was confirmed by the results of a Diabetes Control and Complications Trial published in 1993 that complications tend to occur unless blood glucose level is strictly managed, which led to heightened awareness of simple blood glucose level measurement systems that make use of biosensor systems in clinical medicine. This heightened awareness has led to greater prescription of simple blood glucose level measurement systems to diabetes patients, and even among patients who had never before measured their own blood glucose, there was greater interest in measurement of their own blood (see Non-Patent Document 20).

In 1996, Hill et al. disclosed a strip electrode that involved screen printing. This strip was equipped with a slender support, and this support included first and second conductors that extended along said support. With the biosensor of Hill et al., an active electrode is disposed so as to be in contact with a liquid mixture and the first conductor. An electron transfer substance and an enzyme capable of exerting a catalytic action in the reaction are deposited on this active electrode. A reference electrode is disposed so as to be in contact with the mixture and the second conductor (see, for example, Patent Documents 41, 52, 54, and 60).

To manufacture a biosensor with good measurement accuracy and without variance between products, it is extremely important that the reaction reagent be disposed accurately in a specified location on the biosensor. In view of this, in 1980 Pace et al., and in 1994 Pollman et al., proposed the use of punching technology to form a reagent well including a wall for holding or fixing a reaction reagent at a specific location on a biosensor until the reaction reagent has dried (see Patent Documents 15 and 35).

Nevertheless, such biosensor manufacturing methods generally increase the number of members entailed, and each member needs to be machined very precisely. As a result, the manufacturing process becomes more complicated, and this leads to the problems of lower manufacturing efficiency and higher costs.

In 1990 and 1991, Weetall et al. reported on a well-type biosensor in which electrodes and a reaction reagent were disposed in a well provided to a base plate (see Patent Documents 22 and 24).

This biosensor is a type with which a liquid sample is dropped perpendicularly to the depth direction of the well, making it difficult for the user to use. Also, since the electrodes and the reaction reagent layer have a complicated structure, the cost is higher, so a disadvantage is that this approach is not suited to mass production.

In 1996, Yoshioka et al. proposed the following as a simpler method for manufacturing a biosensor with less variance between products and which was capable of more accurate measurement. In the manufacture of a biosensor comprising an insulating base plate, a working electrode, and a counter electrode, the electrodes were formed in a substantially circular shape, so that when the reaction reagent was applied, a reagent layer could be formed more simply and accurately at the desired locations on the electrodes. The aim of this method is to increase the accuracy of the measurement system itself, and to make the manufacturing processing easier (see Patent Document 42).

In 2001, Winarta et al. reported on a technique for delineating the electrode area where a reaction reagent is disposed on a biosensor. They delineated the electrode area by forming rectangular, square, or circular cuts in a base plate with a carbon dioxide laser, and laminating the resulting plate over a bottom plate. They further held the reaction reagent in an electrode area delineated by the cuts (see Patent Document 67).

However, this method is similar to the above-mentioned methods of Pace et al. and Pollmann et al. in that the number of necessary members is increased and the various members have to be machined very precisely. Therefore, this method also makes the manufacturing process more complicated, the manufacturing efficiency is poor, and the costs are higher.

Other methods that do not involve the use of a well have also been reported as a method for specifying the reaction reagent distribution and the position of the reaction reagent on the biosensor. As an example of this, Bhullar et al. have proposed the following biosensor (see Patent Documents 71, 74, 79, 82, and 85). With this biosensor, a conductive track is formed on a base plate, and an electrode array is formed by this track. A recess is formed near the electrode array on the same base plate. This biosensor also comprises a plate that is disposed on the same base plate, so as to be opposite the surface on which the electrode array and the recess are formed.

With this constitution, the reaction reagent placed on the electrode array spreads over the entire electrode array until it reaches the recess. When the reaction reagent liquid reaches the end of the recess, the interface energy in between the plate and the electrode array falls below the surface tension of the reaction reagent liquid, so the reaction reagent liquid is held on the electrode array. Also, since the reaction reagent liquid is drawn along the edges of the recess, the recess facilitates the diffusion of the reaction reagent liquid on the electrode array.

Compared to the method of Yoshioka et al., the manufacturing method of Bhullar et al. requires an extra machining step of forming a recess in the base plate in order to specify the place where the reaction reagent is to be disposed. Consequently, this method entails more equipment the number of steps increases, and greater machining precision is necessary, so it seems unsuited to the large-scale manufacture of inexpensive biosensors.

As for disposable biosensors, there has not only been technological development of the structure, but measurement methods have also been the focus of considerable technological development. Ikeda et al. in a 1996 report presented a measurement method aimed at higher accuracy. This report deals with a method for quantifying a specific target substance in a liquid sample by using a biosensor having an insulating plate, a working electrode, a counter electrode, and a reaction layer containing an enzyme, in which the liquid sample is drawn into the biosensor, after which the working electrode and the counter electrode are short circuited before the application of voltage for measuring the specific target substance, which eliminates measurement error due to uneven dissolution of the reaction layer, and allows more accurate measurement to be performed (see Patent Document 44).

In 1996, Ikeda et al. disclosed a biosensor comprising a liquid sample detection electrode at a position within a liquid sample chamber and away from a liquid sample intake port. That is, this liquid sample detection electrode is the last to touch the liquid sample of all the electrodes disposed in the liquid sample chamber. Therefore, the fact that a liquid sample is detected by the liquid sample detection electrode means that the liquid sample has diffused over the electrodes (working electrode, counter electrode, etc.) that are important for measurement. With this biosensors, measurement can be commenced after confirming that the liquid sample has thus diffused to the electrodes that are important for measurement (see, for example, Patent Documents 46 and 50).

In 1997, Carter et al. disclosed an electrode strip comprising an electrode support, a reference or counter electrode disposed on the electrode support, a working electrode provided a specific distance away from the reference or counter electrode, a covering layer that defines an enclosed space covering the reference and working electrodes and that has an aperture for receiving a sample into said enclosed space, and a plurality of mesh layers interposed in the enclosed space between the covering layer and the support. This covering layer has a sample application opening provided a specific distance from the electrodes. The working electrode contains an enzyme which can exert a catalytic action on a reaction involving its own substrate, and an electron transfer substance which can transfer electrons between the enzyme-catalyzed reaction and the working electrode. Carter et al. stated that this apparatus reduces the effect of hematocrit on a sensor reading. According to this disclosure, this is accomplished by a combination of the thin layer of the sample solution created by the mesh layers and the position where the reference electrode is disposed with respect to the working electrode (see Patent Document 49).

In 1998, MacAleer et al. disclosed a disposable glucose test strip comprising a plate, a reference electrode, a working electrode, and means for making an electrical connection. The above-mentioned working electrode has a conductive base layer and a covering layer provided covering the conductive base layer. This covering layer is a filler that has both hydrophobic and hydrophilic surface regions forming a network, an enzyme, and an electron transfer substance. The measurement result obtained using this biosensor is not affected by the ambient temperature where the biosensor is used, and exhibits no sensitivity to hematocrit (see Patent Document 53).

In 1998, Henning et al. disclosed a biosensor with which the effect of interfering substances could be reduced. This apparatus generally comprises an electrode for electrochemically measuring the concentration of a target substance in a solution. This apparatus includes peroxidase that is covalently linked to fine particles of carbon and is held in a matrix in a state of close contact with the electrode. With this apparatus, the enzyme/fine particles reduce the effect of known interfering substances of carbon (see Patent Document 55).

In 1998, Charlton et al. disclosed a biosensor having an insulating base plate equipped with an electrode on its surface which reacts with a specimen to produce mobile electrons. This base plate is joined with a cover composed of a deformable material, and has a concave area surrounded by a flat surface so as to form a liquid sample chamber into which a liquid sample can flow. The side of the lid facing the base plate is covered with a polymer material, and the work of this polymer material bonds the lid to the base plate and increases the hydrophilic nature of the capillary space (see Patent Documents 57 and 59).

This biosensor of Charlton et al. works the same as the above-mentioned biosensor equipped with a spacer and cover disclosed by Nankai et al., but its constitution is different, and since there are fewer difficult steps and materials, it is much more likely that this biosensor can be mass-produced inexpensively. However, in the manufacture of this biosensor, selecting the cover material and manufacturing accuracy are extremely important, and difficulties are foreseen in these areas.

In 1998, Pritchard et al. disclosed a biosensor in which the minimum amount of blood sample was only about 9 μL. The main feature of this biosensor is that a working electrode and counter electrode that are substantially the same size and are composed of the same conductive substance are held on a base plate, and these electrodes are covered with an upper cover equipped with a cut-out forming a reagent well. This cut-out exposes a smaller area of the counter electrode than the working electrode. A reagent substantially covers the exposed areas of the working electrode and counter electrode in the reagent well. A mesh that is impregnated with a surfactant covers the reagent well and is affixed to the upper cover (see Patent Document 58). However, even at the time this invention was disclosed, 9 μL was twice the amount of blood as that in the above-mentioned invention of Nankai et al., and this invention was unsuited to reducing the amount of sample needed for measurement.

In 1999, Hoenes et al. reported on a measurement method for simultaneously performing calorimetric and electrochemical measurement, in order to ameliorate the disadvantage of colorimetric detection and reaction. This disadvantage is that while colorimetric detection and reaction is useful at low concentrations of the measurement target substance, measurement is difficult at higher concentrations. The method proposed by Hoenes et al. is as follows. An oxidizing enzyme and a chromogen A that accepts electrons from the enzyme are used in measurement. The chromogen A is reduced to a compound A', after which a coupling reaction with a substance BX is conducted to form a colored reagent A'B. The concentration of this A'B is measured calorimetrically as an index of the presence or amount of the measurement target substance. Also, since an electrochemically measurable atom group X' is cleaved off from BX by the coupling reaction, the concentration of this X' is measured electrochemically as an index of the amount of the measurement target substance. Hoenes et al. thus performed colorimetric and electrochemical measurement of the target substance simultaneously (see Patent Document 61).

Nevertheless, to realize this system, the configuration of the biosensor and measurement apparatus would probably be extremely complicated. And this system can not provide merits (such as measurement accuracy) that offsets this complexity. Also, with an electron transfer system that follows an enzyme reaction, since the reaction reagent composition and the reaction system are complicated, it can be easily imagined that the response speed and reproducibility of the resulting response values will suffer, as will the storage stability of the biosensor.

In 1999, Crismore et al. disclosed a biosensor in which a window is provided to the liquid sample chamber. The main feature of this biosensor is that because a window that is transparent with respect to a colored upper cover is employed for the liquid sample chamber, the user can confirm that enough blood for measurement has been drawn into the liquid sample chamber. Also, if a notch is added to the base plate at the intake port, the intake of the liquid sample can be carried out more smoothly (see Patent Document 62).

But at the time this invention was disclosed, Ikeda et al. had already reported a system in which a measurement device electrochemically detects that a sufficient quantity of liquid sample has been drawn into the liquid sample chamber.

From the 1980's and into the 1990's, screen printing to which printed plate manufacturing technology was applied was used to manufacture biosensors. From about the mid-1990's until the late 1990's, precision machining technology came to be used as the method for manufacturing biosensors to reduce variance between manufacturing lots.

With a biosensor in which the electrodes are formed by screen printing, variance occurs in the surface area of the measuring electrodes due to the bleeding of conductive paste during printing, and this adversely affects the response characteristics. Fujiwara et al. reported on a method of producing a biosensor with good accuracy and by a simple production process instead of using screen printing. This manufacturing method involved forming a metal film over the entire surface of an insulating plate, then dividing the metal film by forming slits, providing a measuring electrode and a counter electrode to which liquid sample is applied and a cover that forms a lead for applying voltage to these electrodes, and covering the measuring electrode and the counter electrode with a reagent layer (see Patent Documents 63 and 69).

With the method of Fujiwara et al., the measuring electrode and the counter electrode are produced by forming slits with a laser or the like in a metal film formed by through vapor deposition, sputtering, or by bonding a metal foil over an insulating plate. Accordingly, there is no bleeding of the print as in screen printing, and the surface area of the electrodes can be accurately defined. Therefore, there is less variance in response characteristics among sensors, and a biosensor with good precision can be obtained.

Advantages to laser machining are that the manufacturing steps and the required equipment are not complicated, manufacturing reproducibility is good, and so forth, and this machining is extremely useful in the manufacture of biosensors. The working of a metal film on an insulator is a technique applied in many fields other than biosensors, and its usefulness has been corroborated in numerous reports (see, for example, Patent Documents 25, 43, 45, 47, and 56).

Also, from 2000 onward, there have been reports of applying precision machining by laser in the field of biosensor manufacturing technology. These include a method for forming an electrode by laser machining of a metal layer on an insulating plate (see Patent Documents 81, 84, and 87).

There have been many reports up to now concerning the development of systems for measuring with greater accuracy. These relate to the structure of a biosensor, or relate to a manufacturing method, or relate to a measurement method. All current biosensors, however, still have various drawbacks.

One of these drawbacks is interference with the biosensor reading brought about by other substances which are present in a liquid sample and can oxidize at the same potential as the measurement target. These are referred to as interference substances in this Specification, and typical examples include ascorbic acid, uric acid, and acetaminophen. When these and other interference substances oxidize, the current produced by their oxidation is on top of the current intrinsic to the measurement target, and cannot be distinguished from the current intrinsic to the measurement target, so the concentration thereof is estimated too high. As a result, accuracy drops in the quantification of the measurement target substance in the liquid sample.

The 2001 report by Ikeda et al. proposed a method for reducing the effect of interference substances. The biosensor of Ikeda et al. had a working electrode, a counter electrode and a reagent layer, and had a third electrode not in contact with the reagent layer, in order to reduce the decrease in measurement accuracy caused by interference substances. Ikeda et al. aimed to reduce the effect of interference substances by using this third electrode as an interference substance detection electrode (see Patent Document 65).

Another drawback to biosensors in which the liquid sample is blood is interference caused by red blood cells (hematocrit effect). This interference tends to result in an apparently high reaction rate with respect to a low hematocrit level, or conversely, to result in an apparently low reaction rate with respect to a high hematocrit level.

In 1984, Vogel et al. reported on a biosensor in which glass fibers were deposited as a technique for reducing the hematocrit effect. This biosensor separated or removed red blood cell from blood by passage of blood through glass fibers. Whereas red blood cells were usually separated or removed by centrifuging, with this method, red blood cells could be separated without pretreatment, but the deposition of glass fibers is expected to drive up material costs and manufacturing costs, and to adversely affect manufacturing precision. In addition, since blood is passed through fibers whose diameter is sufficient to separate red blood cells, the rate at which the sample is drawn in is low, and this probably makes the product less convenient to use.

Also, in 2001, Winarta et al. reported on the composition of a reaction reagent that reacts with a measurement target substance. In this report, a polymer stabilizer, a binder, and a surfactant are added along with an enzyme and an electron transfer substance to the reaction reagent (see Patent Document 66).

However, adding these substances to the reaction reagent causes problems in that it makes the reagent preparation process more complicated, makes the reagent layer formation process more complicated by increasing the reaction reagent viscosity, adversely affects the drying process, leads to a decrease in the reaction reagent reaction efficiency, decreases the long-term storage stability of the reaction reagent, and so forth.

In addition to the above drawbacks, other drawbacks to prior art are that its linear range is limited, and that a relatively large quantity of sample is needed. Furthermore, these apparatus take a comparatively long time until the steady response prior to obtaining a reading becomes obvious. Each of these drawbacks individually, or combined with one or more other drawbacks, can be a source of an erroneous measurement reading in analysis. In preliminary tests conducted by the inventors of the present invention, prior art that claimed to reduce the effect of hematocrit on a glucose reading was limited to a low glucose concentration, and indicated that there was an effect only at a low glucose concentration. At the higher blood glucose levels that actual diabetes patients can display, the desired effect is not exhibited.

Technology aimed at reducing the volume of liquid sample necessary for measurement in an attempt to make the product more convenient to use for the user has been reported up to now. For instance, there have been various studies into sensor structure, and particularly the structure of the liquid sample chamber, or electrode layout, reaction reagent composition and additives, measurement methods, and so forth (see, for example, Patent Documents 68, 70, 72, 75, 77, and 78).

Even if the minimum amount of liquid sample needed is reduced, though, the puncturing that causes the user pain is still not eliminated. Also, if the required amount is reduced so much that the space inside the liquid sample chamber is filled with the reagent layer, this will likely have a detrimental effect on how the liquid sample is drawn in. Also, if the liquid sample chamber is merely made smaller to reduce the required amount, then the electrode surface area and the reagent layer will also become smaller at the same time, so the response value obtained during measurement will be smaller, and as a result, the signal to noise ratio (S/N ratio) will deteriorate and measurement accuracy will suffer.

Recent developments of biosensors have often attempted to enhance both convenience and accuracy. Of these attempts, particular emphasis has been placed on shortening the measurement time and reducing the amount of liquid sample required for measurement.

In measurement with a biosensor, the reaction reagent disposed in a dry state must be redissolved by the blood or other liquid sample. Therefore, to shorten the measurement time, fast reactivity is necessary, and higher resolubility of the reaction reagent can be considered an advantage. A problem with a reaction reagent with excellent resolubility, however, is that the reagent ends up being carried away in the intake direction when the liquid sample is drawn in. If the reaction reagent is carried away, this decreases the reaction reagent concentration in the reaction area, so the measured value will be lower than the true value. Also, if the intake rate should change due to action on the part of the user or the hematocrit value, the reaction reagent concentration in the reaction area will also change, so measurement reproducibility is greatly diminished.

This problem has become much more critical as biosensor development has advanced in recent years. Methods in which a reaction reagent is fixed on an electrode using a polymer or a sol-gel matrix have been reported as a method for forming a reaction reagent layer that is not carried away (see Patent Documents 31, 33, 34, 36, 48, and 51).

These reports involve the use of an electron transfer substance that is non-leachable and non-diffusible. However, when the leaching or diffusion of a reaction reagent is suppressed by adding a polymer to the reaction reagent, or by fixing with covalent bonds, or by supporting the reaction reagent in a sol-gel matrix, it becomes impossible to conduct a fast reaction within a limited amount of time. This is contrary to the biosensor development trend of recent years, which is to try and shorten measurement time.

In 2004, Bhullar et al. reported an attempt to achieve a suitably controlled flow of liquid sample by forming a microstructure by working the basal part of an intake port distal end (see Patent Documents 80 and 83).

In these reports, the flow of liquid sample is adjusted by capillary force during liquid sample intake. However, even though the direction in which the liquid sample flows can be controlled, the intake rate cannot be controlled, and it is difficult to prevent the reaction reagent from being carried away. Also, in these reports, the base plate is worked by laser ablation, but this requires sophisticated machining technology and considerable equipment to form a microstructure such as that proposed. Putting this technique into actual practice is probably going to be met with many difficulties.

An example of working a base plate into a groove shape is the report of Say et al. Their report is aimed at a biosensor implanted in subcutaneous interstitial tissue of the patient, and the base plate is worked into a groove shape, and a conductive substance is placed in the groove thus formed, thereby forming an embedded electrode (see Patent Documents 64, 73, and 86).

The basic structure of a biosensor in which a reaction reagent is disposed on this embedded electrode is not that different from the structure of a conventional embedded electrode, so this does not seem to solve the problem of controlling the extent to which the reaction reagent is carried away by liquid sample intake. Also, with biosensors that are expected to see use under a variety of conditions, the flexibility of the base plate in these biosensors is predicted to be affected by the usage environment, which will likely pose problems in practical application.

In the embodiments given in the 2003 report of Feldman et al., a groove is formed in a biosensor by subjecting the base plate to embossing (see Patent Document 76).

In this case, the opposite side of the base plate on which the groove is formed by embossing ends up being worked into a peaked shape. This portion is the portion that comes into direct contact with user when the user mounts the biosensor in the measurement device, so the product is obviously less comfortable to use if the shape is peaked. Also, if the peaked portion should be deformed during transport or when touched by the user, the groove shape and volume may be changed, and this could have a serious adverse affect on measurement accuracy. Furthermore, embossing requires that the material be carefully selected as well. For the above reasons, it is believed that there are still problems with this technique if the convenience and measurement accuracy demanded of a biosensor are both to be satisfied.

In 2006, Huang reported on an embedded electrode type of biosensor in which a liquid sample chamber was formed by providing a recess to the base plate (see Patent Document 88).

With this biosensor, the electrode is embedded in a hole in the base plate, and a liquid sample chamber is not formed by laminating a spacer over the base plate, but rather by providing a recess to the base plate. This reduces the number of parts needed for manufacturing a biosensor, but high precision is required of the recess formation because the shape of recess defines the shape and volume of the liquid sample chamber. Also, since the basic structure of the liquid sample chamber is not that different from a conventional design, this does not seem to solve the problem of controlling the extent to which the reaction reagent is carried away by liquid sample intake.

These biosensors are sensors that make use of the molecular recognition capability of biological materials such as microbes, enzymes, antibodies, and nucleic acids. Specifically, they make use of various kinds of biochemical reactions that occur when a biological material recognizes the specific component being targeted, such as the consumption of oxygen by the respiration of microorganisms, an enzyme reaction, coloration by a coloring reagent, or the like. Research and application of biosensors utilizing enzymes have been particularly active, and these have seen practical use in the medical field and food industry. Of these, biosensors used in the medical field are used by diabetes patients to measure their own blood glucose levels, and are sold around the world.

The following is a list of US patent documents, Japanese patent documents, and non-patent documents cited in this Specification.

Patent Document 1: U.S. Pat. No. 2,913,386, November 1959, Clark
Patent Document 2: U.S. Pat. No. 3,539,455, November 1970, Clark
Patent Document 3: U.S. Pat. No. 3,542,662, November 1970, Hicks et al.
Patent Document 4: U.S. Pat. No. 3,770,607, November 1973, William
Patent Document 5: U.S. Pat. No. 3,788,950, January 1974, Hicks et al.
Patent Document 6: U.S. Pat. No. 3,836,003, September 1974, Mindt et al.
Patent Document 7: U.S. Pat. No. 3,838,033, September 1974, Mindt et al.
Patent Document 8: U.S. Pat. No. 3,948,745, April 1976, Guilbault et al.
Patent Document 9: U.S. Pat. No. 3,979,274, September 1976, Newman et al.
Patent Document 10: U.S. Pat. No. 4,073,713, February 1978, Newman et al.
Patent Document 11: U.S. Pat. No. 4,085,009, April 1978, Pace
Patent Document 12: U.S. Pat. No. 4,092,233, May 1978, Clemens et al.
Patent Document 13: U.S. Pat. No. 4,100,029, July 1978, Prosper
Patent Document 14: U.S. Pat. No. 4,224,125, September 1978, Nankai et al.
Patent Document 15: U.S. Pat. No. 4,225,410, September 1980, Pace et al.
Patent Document 16: U.S. Pat. No. 4,454,007, June 1984, Pace
Patent Document 17: U.S. Pat. No. 4,477,575, October 1984, Vogel et al.
Patent Document 18: U.S. Pat. No. 4,534,356, August 1985, Papadakis
Patent Document 19: U.S. Pat. No. 4,545,382, October 1985, Higgins et al.
Patent Document 20: U.S. Pat. No. 4,711,245, December 1987, Higgins et al.
Patent Document 21: U.S. Pat. No. 4,897,173, January 1990, Nankai et al.
Patent Document 22: U.S. Pat. No. 4,963,245, October 1990, Weetall et al.
Patent Document 23: U.S. Pat. No. 4,975,175, December 1990, Karube et al.
Patent Document 24: U.S. Pat. No. 5,066,372, November 1991, Weetall et al.
Patent Document 25: U.S. Pat. No. 5,104,480, April 1992, Wojnarowski et al.
Patent Document 26: U.S. Pat. No. 5,120,420, June 1992, Nankai et al.
Patent Document 27: U.S. Pat. No. 5,120,420, June 1992, Nankai et al.
Patent Document 28: U.S. Pat. No. 5,126,034, June 1992, Carter et al.
Patent Document 29: U.S. Pat. No. 5,185,256, February 1993, Nankai et al.
Patent Document 30: U.S. Pat. No. 5,229,282, July 1993, Yoshioka et al.
Patent Document 31: U.S. Pat. No. 5,262,035, November 1993, Gregg et al.
Patent Document 32: U.S. Pat. No. 5,264,103, November 1993, Yoshioka et al.
Patent Document 33: U.S. Pat. No. 5,264,104, November 1993, Gregg et al.
Patent Document 34: U.S. Pat. No. 5,264,105, November 1993, Gregg et al.
Patent Document 35: U.S. Pat. No. 5,288,636, February 1994, Pollmann et al.
Patent Document 36: U.S. Pat. No. 5,320,725, June 1994, Gregg et al.
Patent Document 37: U.S. Pat. No. 5,320,732, June 1994, Nankai et al.
Patent Document 38: U.S. Pat. No. 5,385,846, January 1995, Kuhn et al.
Patent Document 39: U.S. Pat. No. 5,405,511, April 1995, White et al.
Patent Document 40: U.S. Pat. No. 5,438,271, August 1995, White et al.
Patent Document 41: U.S. Pat. No. 5,509,410, April 1996, Hill et al.

Patent Document 42: U.S. Pat. No. 5,512,159, April 1996, Yoshioka et al.
Patent Document 43: U.S. Pat. No. 5,512,489, April 1996, Girault et al.
Patent Document 44: U.S. Pat. No. 5,565,085, October 1996, Ikeda et al.
Patent Document 45: U.S. Pat. No. 5,576,073, November 1996, Kickelhain et al.
Patent Document 46: U.S. Pat. No. 5,582,697, December 1996, Ikeda et al.
Patent Document 47: U.S. Pat. No. 5,593,739, January 1997, Kickelhain et al.
Patent Document 48: U.S. Pat. No. 5,593,852, January 1997, Heller et al.
Patent Document 49: U.S. Pat. No. 5,628,890, May 1997, Carter et al.
Patent Document 50: U.S. Pat. No. 5,650,062, July 1997, Ikeda et al.
Patent Document 51: U.S. Pat. No. 5,665,222, September 1997, Heller et al.
Patent Document 52: U.S. Pat. No. 5,682,884, November 1997, Hill et al.
Patent Document 53: U.S. Pat. No. 5,708,247, January 1998, MacAleer et al.
Patent Document 54: U.S. Pat. No. 5,727,548, March 1998, Hill et al.
Patent Document 55: U.S. Pat. No. 5,755,953, May 1998, Henning et al.
Patent Document 56: U.S. Pat. No. 5,758,398, June 1998, Rijnbeek et al.
Patent Document 57: U.S. Pat. No. 5,759,364, June 1998, Charlton et al.
Patent Document 58: U.S. Pat. No. 5,762,770, June 1998, Pritchard et al.
Patent Document 59: U.S. Pat. No. 5,798,031, August 1998, Charlton et al.
Patent Document 60: U.S. Pat. No. 5,820,551, October 1998, Hill et al.
Patent Document 61: U.S. Pat. No. 5,858,691, January 1999, Hoenes et al.
Patent Document 62: U.S. Pat. No. 5,997,817, December 1999, Crismore et al.
Patent Document 63: U.S. Pat. No. 6,004,441, December 1999, Fujiwara et al.
Patent Document 64: U.S. Pat. No. 6,103,033, August 2000, Say et al.
Patent Document 65: U.S. Pat. No. 6,212,417, April 2001, Ikeda et al.
Patent Document 66: U.S. Pat. No. 6,258,229, July 2001, Winarta et al.
Patent Document 67: U.S. Pat. No. 6,287,451, September 2001, Winarta et al.
Patent Document 68: U.S. Pat. No. 6,299,757, October 2001, Feldman et al.
Patent Document 69: U.S. Pat. No. 6,309,526 October 2001 Fujiwara et al.
Patent Document 70: U.S. Pat. No. 6,338,790, January 2002, Feldman et al.
Patent Document 71: U.S. Pat. No. 6,447,657, September 2002, Bhullar et al.
Patent Document 72: U.S. Pat. No. 6,461,496, October 2002, Feldman et al.
Patent Document 73: U.S. Pat. No. 6,484,046, November 2002, Say et al.
Patent Document 74: U.S. Pat. No. 6,540,890, April 2003, Bhullar et al.
Patent Document 75: U.S. Pat. No. 6,576,101, June 2003, Heller et al.
Patent Document 76: U.S. Pat. No. 6,592,745, July 2003, Feldman et al.
Patent Document 77: U.S. Pat. No. 6,616,819, September 2003, Liamos et al.
Patent Document 78: U.S. Pat. No. 6,618,934, September 2003, Feldman
Patent Document 79: U.S. Pat. No. 6,645,359, November 2003, Bhullar et al.
Patent Document 80: U.S. Pat. No. 6,755,949, June 2004, Bhullar et al.
Patent Document 81: U.S. Pat. No. 6,767,440, July 2004, Bhullar et al.
Patent Document 82: U.S. Pat. No. 6,814,843, November 2004, Bhullar et al.
Patent Document 83: U.S. Pat. No. 6,814,844, November 2004, Bhullar et al.
Patent Document 84: U.S. Pat. No. 6,866,758, March 2005, Bhullar et al.
Patent Document 85: U.S. Pat. No. 6,911,621, June 2005, Bhullar et al.
Patent Document 86: U.S. Pat. No. 7,003,340, February 2006, Say et al.
Patent Document 87: U.S. Pat. No. 7,073,246, July 2006, Bhullar et al.
Patent Document 88: U.S. Laid-Open Patent Application No. 2006/0175199, August 2006, Huang
Patent Document 89: Japanese Patent Publication No. H4-6907 (Japanese Laid-Open Patent Application No. S59-166852), February 1992, Kawaguri et al.
Non-Patent Document 1: L. C. Clark, Jr., "Monitor and control of blood and tissue oxygenation," *Trans. Am. Soc. Artif. Intern. Organs,* 1956 2, 41.
Non-Patent Document 2: L. C. Clark, Jr., "Electrode system for continuous monitoring in cardiovascular surgery," *Ann. NY Acad. Sci,.* 1962 102:29/45.
Non-Patent Document 3: Voss D O., "A new oxygen electrode model for the polarographic assay of cellular and mitochondrial respiration," *Anal Biochem.* Sep. 6, 1963; 211-222.
Non-Patent Document 4: Updike, S J. et al., "The enzyme electrode," *Nature* Jun. 3, 1967; 214(5092): 986-988.
Non-Patent Document 5: Fujihira et al., "Reversible redox titrations of cytochrome c and cytochrome c oxidase using detergent solubilized electrochemically generated mediator-titrations," *Biochemical and Biophysical Research Communications* 1974 61(2): 538-543.
Non-Patent Document 6: Divies, C., "Remarks on ethanol oxidation by an 'Acetobacter xylinum' microbial electrode," *Ann Microbiol* (Paris), 1975 February-March; 126(2): 175-86. (Original text in French, and this title is an English translation by the author.)
Non-Patent Document 7: L. C. Thomas et al., "Voltammetric measurement of reduced Nicotinamide-Ademine Nucleotides and application to amperometric measurements of enzyme reactions," *Analytica Chemica Acta* 1975, 78, 271-276.
Non-Patent Document 8: Yagi et al., "A new assay method for hydrogenase based on an enzymic electrode reaction. The enzymic electric cell method," *J Biochem.* 1975 September; 78 (3): 443-454.
Non-Patent Document 9: Johnson, J M. et al., "Metal complex as mediator-titrants for electrochemical studies of biological systems," *Anal. Biochem.* 1983 August; 133 (1): 186-189.

Non-Patent Document 10: Cass et al., "Ferrocene-mediated enzyme electrode for amperometric determination of glucose," *Ana. Chem.* 1984 April; 56 (4): 667-671.

Non-Patent Document 11: Denis, C. et al., "Use of the LA 640 for a simple method of measuring the concentration of muscle lactate" J Physiol. 1985; 80(3): 168-172.

Non-Patent Document 12: D'Costa, E. J. et al., "Quinoprotein glucose dehydrogenase and its applications in an amperometric glucose sensor," *Biosensors* 1986 2: 71-87.

Non-Patent Document 13: Cass et al., "Biosensors: Fundamentals and Applications," Oxford University Press, 1987 & 1989.

Non-Patent Document 14: Denis, C. et al., "Effects of endurance training on hyperammonaemia during a 45-min constant exercise intensity," *Eur J Appl Physiol Occup Physiol.* 1989; 59 (4): 268-272.

Non-Patent Document 15: Morris, N. A. et al., "Electrochemical capillary fill device for the analysis of glucose incorporating glucose oxidase and ruthenium(III) hexamine as mediator," *Electroanalysis* 1992 4: 1-9.

Non-Patent Document 16: The Diabetes Control and Complications Trial Research Group, "The Effect of Intensive Treatment of Diabetes on the Development and Progression of Long-Term Complications in Insulin-Dependent Diabetes Mellitus," *New England Journal of Medicine*, Sep. 30, 1993 329 (14) 977-986.

Non-Patent Document 17: Loughran, M. G. et al., "Amperometric detection of histamine at a quinoprotein dehydrogenase enzyme electrode," *Biosensors and Bioelectronics*, 1995 10: 569-576.

Non-Patent Document 18: Loughran, M. G. et al., "Ammonium requirement and stability of methanol dehydrogenase TTF. TCNQ electrodes," *The Analyst,* 1996 121: 1711-1715.

Non-Patent Document 19: Loughran, M. G. et al., "Development of apyrroloquinoline quinone (PQQ) mediated glucose oxidase enzyme electrode for detection of glucose in fruit juice," *Electroanalysis,* 1996 8 (10) 870-875.

Non-Patent Document 20: Newman, J D. et al., "Home blood glucose biosensors: a commercial perspective," *Biosens Bioelectron.* Jun. 15, 2005; 20 (12): 2435-2453.

SUMMARY OF THE INVENTION

A biosensor according to the first aspect of the present invention is a biosensor that detects a target substance contained in a liquid sample, including an insulating base plate including a recess formed in a portion that is thinner than the surrounding part, a working electrode and a counter electrode, at least one of which is disposed in the recess, and a reaction reagent that is disposed in the recess and reacts with the target substance in the liquid sample.

A method according to the second aspect of the present invention is a method of producing a biosensor, including
forming a recess by reducing the thickness of an insulating base plate,
disposing a working electrode and/or a counter electrode in the recess,
disposing a reaction reagent that reacts with a target substance in the recess,
disposing a spacer on the base plate to expose at least part of the recess, and
disposing an upper cover over the spacer to cover the recess exposed from the spacer.

A detection system according to the third aspect of the present invention is a detection system including: the biosensor according and a detection device to detect a target substance in a liquid sample from the current between the working electrode and the counter electrode of the biosensor.

DETAILED DESCRIPTION OF THE INVENTION

Figure 1:
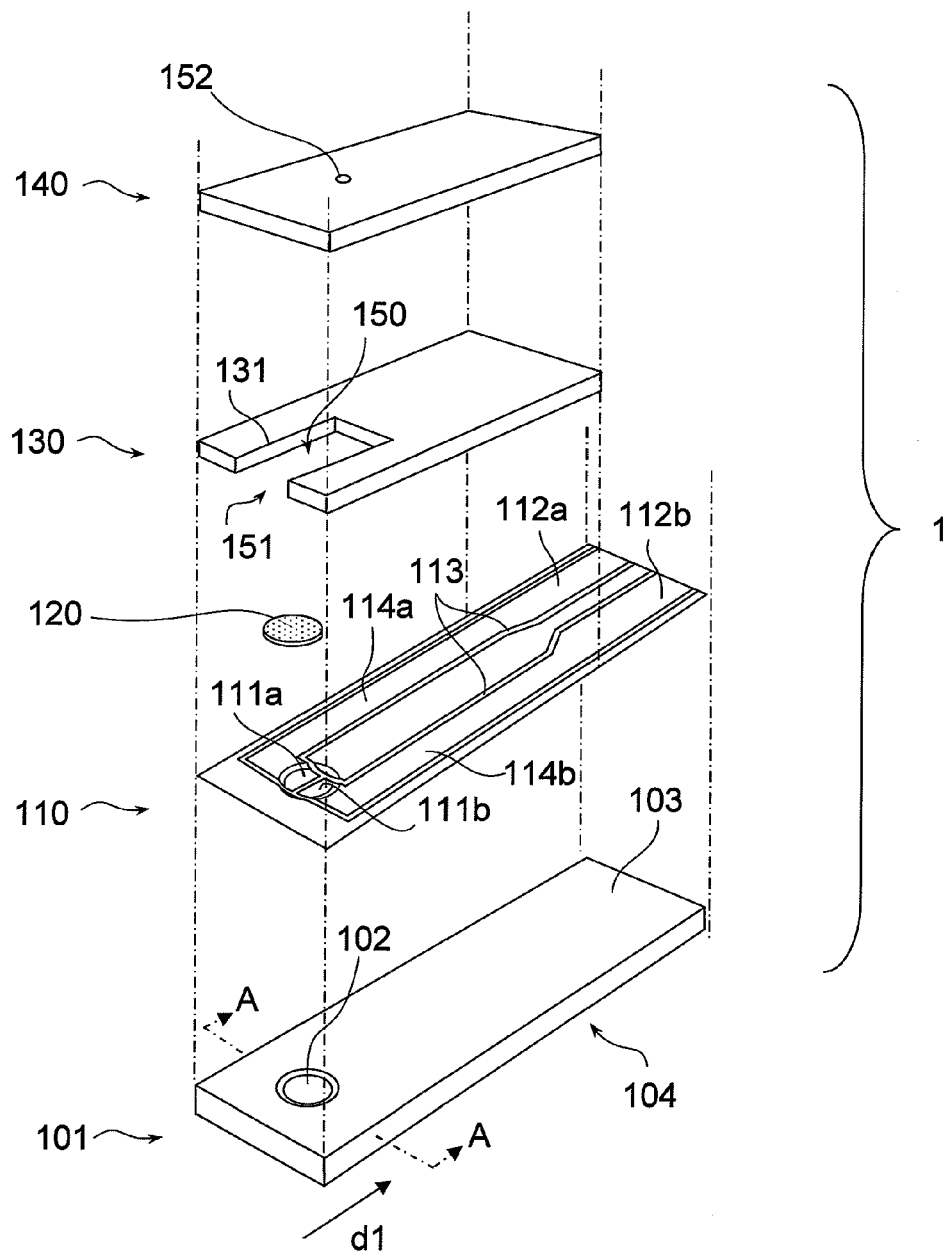
FIG. 1 is an exploded oblique view of the biosensor pertaining to an embodiment of the present invention.

Embodiments of a biosensor, biosensor manufacturing method, and measurement system using a biosensor will now be described in that order through reference to the drawings. The present invention, however, is not limited to or by the following embodiments, and modifications and revisions are possible within the scope of the intent and spirit of the invention stated and defined in the Claims. In the drawings, the scale may not reflect the actual sizes in some cases, in order to improve visibility.

A. Biosensor

(1) Biosensor 1

(1-1) Summary of Structure

Figure 2:
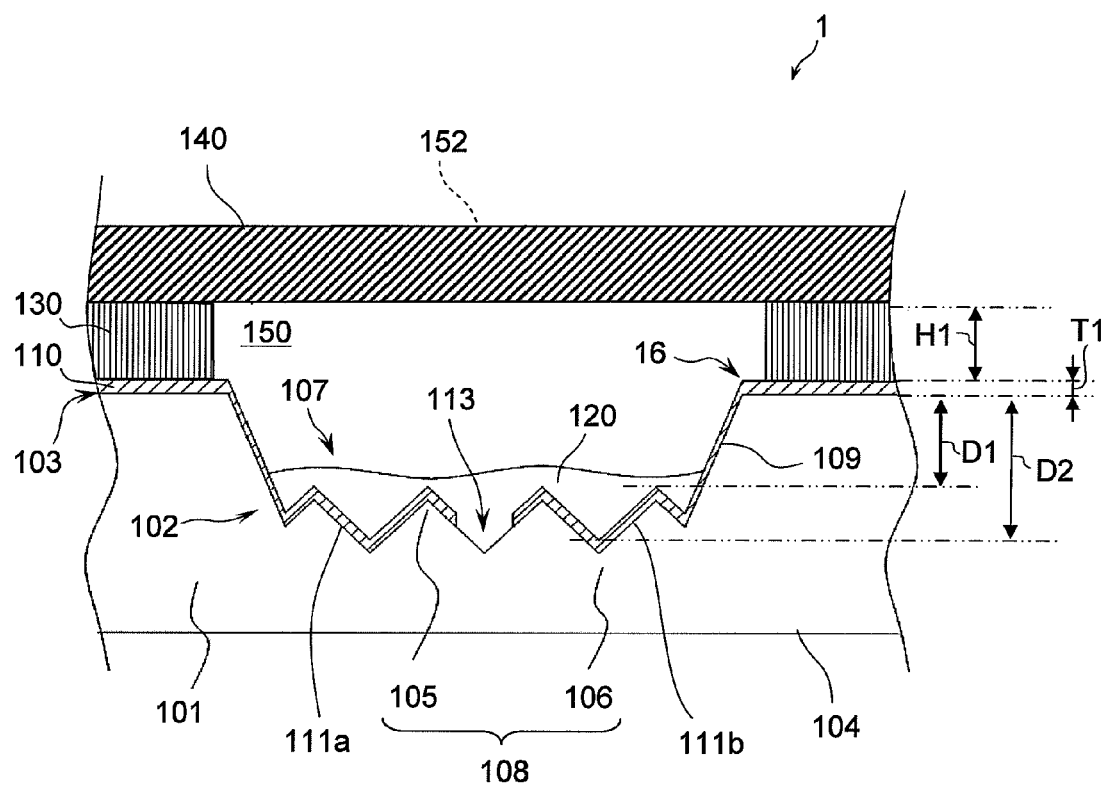
FIG. 2 is a cross section along the A-A line in FIG. 1.

The structure of the biosensor 1, which is an embodiment of the biosensor, will be described through reference to FIGS. 1 and 2. FIG. 1 is an exploded oblique view of the main configuration of the biosensor 1. FIG. 2 is a cross section along the A-A line in FIG. 1.

The biosensor 1 is an example of a biosensor that detects a specific substance in a liquid sample, and is known as an amperometric biosensor. As shown in FIGS. 1 and 2, the biosensor 1 comprises a base plate 101, two electrodes (a working electrode and a counter electrode) 111a and 111b, and a reagent layer 120, which are examples of the insulating base plate, the working electrode, the counter electrode, and the reagent layer, respectively. More specifically, the biosensor 1 comprises the base plate 101, a conductive layer 110, the reagent layer 120, a spacer 130, and an upper cover 140, with these members being stacked in that order.

(1-2) Base Plate 101

As shown in FIG. 1, the base plate 101 is a member in the form of a rectangular board. In the following discussion, the direction parallel to the long sides of the base plate 101 shall be called the X direction, the direction parallel to the short side direction (that is, the direction parallel to the planar orientation of the base plate 101 and perpendicular to the X direction) shall be called the Y direction, and the direction perpendicular to the planar orientation of the base plate 101 (that is, the thickness direction of the base plate 101) shall be called the Z direction. A portion of one of the two sides of the base plate 101 is depressed in the Z direction, creating a recess 102. Hereinafter, of the two sides of the base plate 101, the side where the recess 102 is provided shall be called the first side 103, and the opposite side the second side 104.

The base plate 101 is insulating. There are no particular restrictions on the material that makes up the base plate 101, so long as it is a non-conductive substance. Examples of materials that are non-conductive and have favorable structural characteristics include polyethylene terephthalate, vinyl polymers, polyimide, polyester, styrenics and other such resins, glass, and ceramics.

The form of the recess 102, that is, the shape of the recess 102, the size of the recess 102 in the X-Y plane, the depth in the Z direction, the bottom face structure, and so forth, are suitably set according to the size of a liquid sample chamber 150 (discussed below), the electrodes 111a and 111b, the reagent layer 120, and so forth, the positional relationship to these members, the characteristics of the liquid sample in question, and other such factors, and is not limited to any specific configuration. For example, the shape of the recess 102 in the X-Y plane may be circular as shown in FIG. 1, or may be rectangular or some other shape. The form of the recess 102 will be discussed in detail below.

(1-3) Conductive Layer 110

As shown in FIGS. 1 and 2, the conductive layer 110 is formed in a substantially uniform thickness on the first side 103 of the base plate 101, and comprises the two electrodes 111a and 111b, two terminals 112a and 112b, and two conductive tracks 114a and 114b.

Parts of the electrodes 111a and 111b fall within the recess 102. That is, the two electrodes 111a and 111b are both disposed inside the recess 102. As will be discussed later, a plurality of recesses 102 may be provided, but if there are a plurality of recesses, then two electrodes are provided facing each other inside each recess. Within the recess 102, the electrodes 111a and 111b have a depressed shape that conforms to the shape of the recess 102. Also, the electrodes 111a and 111b are formed so as to conform to the concavo-convex shape with peaks 105 and valleys 106.

The electrodes 111a and 111b create an electric field within the recess 102, and can accept electrical signals produced by a reaction between the target substance and the reaction reagent within the reagent layer 120. In addition to electrical signals produced by a reaction between the target substance and the reaction reagent, the electrodes 111a and 111b can also accept electrical signals generated by other things, such as blood cell components or readily oxidized substances in a liquid sample, and the intake of a liquid sample (not shown).

The conductive tracks 114a and 114b have a shape that extends longer in the lengthwise direction of the rectangular shape of the base plate 101. One conductive track 114a is electrically connected to one electrode 111a and terminal 112a, and the other conductive track 114b is electrically connected to the other electrode 111b and terminal 112b. This configuration could also be said to be such that one end of the conductive track 114a is the electrode 111a and the other end is the terminal 112a, and one end of the other conductive track 114b is the electrode 111b and the other end is the terminal 112b. It could also be said that the electrodes, terminals, and conductive tracks make up an electrode set. An insulated state is maintained between the conductive tracks 114a and 114b by non-conductive tracks 113.

The electrode set may be formed in the shape of the various components of the electrode set from a conductive material by printing or the like, or the base plate 101 may be covered with a conductive material, and the non-conductive tracks 113 then formed by laser ablation or the like.

There are no particular restrictions on the constituent material of the conductive layer 110, so long as it is a conductive material (a conductive substance). Examples of conductive materials include inorganic conductive substances typified by metals, metal mixtures, alloys, metal oxides, and metal compounds. More specifically, examples include palladium, aluminum, cobalt, copper, gallium, gold, indium, iridium, iron, lead, magnesium, mercury, nickel, niobium, osmium, platinum, rhenium, rhodium, selenium, silicon, silver, tantalum, tin, titanium, tungsten, uranium, vanadium, zinc, zirconium, mixtures and alloys of these, oxides of these, and compounds of these.

Alternatively, an organic conductive substance, such as a hydrocarbon-based conductive polymer or a hetero atom-containing conductive polymer, can be used as the conductive material. Examples of organic conductive substances include carbon, polypyrrole, polyaniline, polythiophene, polythenylenevinylene, polyazulene, polyisothianaphtene, polyacetylene, polyphenylene, polyphenylenevinylene, polyacene, polyphenylacetylene, polydiacetylene, and polynaphthalene. Of these, polythiophene, polypyrrole, polyaniline, and polyacene-based conductive polymers are more practical materials. In addition to what is listed above, various conductive polymers can be used.

For example, Denatron P-502S, which is manufactured as a conductive polymer by Nagase ChemteX, is a polythiophene-based conductive polymer, and is suitable as an electrode material because it has an electron transfer type of mechanism in which a bipolaron (dication) produced on the polythiophene main chain moves within the molecule, and even hops between molecules, so that electricity flows, and this material exhibits stable conductivity.

A combination of these inorganic conductive substances and organic conductive substances may also be used as the conductive material.

(1-4) Reagent Layer 120

As shown in FIGS. 1 and 2, the reagent layer 120 is disposed in the recess 102 so as to touch both of the two electrodes 111a and 111b. The reagent layer 120 includes a reaction reagent that reacts with the target substance, and along with the electrodes 111a and 111b functions as an active component 107 of the biosensor 1. The active component 107 is an area that is electrochemically active, and is a portion that reacts with a specific substance in a liquid sample and produces an electrical signal.

The reaction reagent can be suitably changed as dictated by the target substance, and is not limited to any specific substance, but is one that will produce an electrical signal upon reacting with the target substance. For example, an enzyme whose substrate is one or more substances that are to be detected can be used as the reaction reagent. Of the various enzymes, a redox enzyme can be used to particular advantage. When the target substance is glucose, examples of such enzymes include glucose oxidase and glucose dehydrogenase; when the target substance is lactic acid include, the examples include lactate oxidase and lactate dehydrogenase; when the target substance is cholesterol, examples include cholesterol esterase and cholesterol oxidase; when the target substance is an alcohol, examples include alcohol oxidase; and when the target substance is bilirubin, examples include bilirubin oxidase. The enzyme used as the reaction reagent is suitably selected according to the target substance, and is not limited to those listed above. Other examples of the target substance besides these include triglycerides and urea.

Also, the reagent layer 120 preferably contains an electron transfer substance along with an enzyme. An electron transfer substance is generally called a "mediator," and is a substance that, either directly or in conjunction with another electron transfer substance, can mediate electron movement, in which electrons of a certain type of reductant or free electrons of a metal or the like move to another certain type of oxidant or metal. A mediator is a substance that reversibly becomes an oxidant and a reductant on the electrodes.

Figure 3:
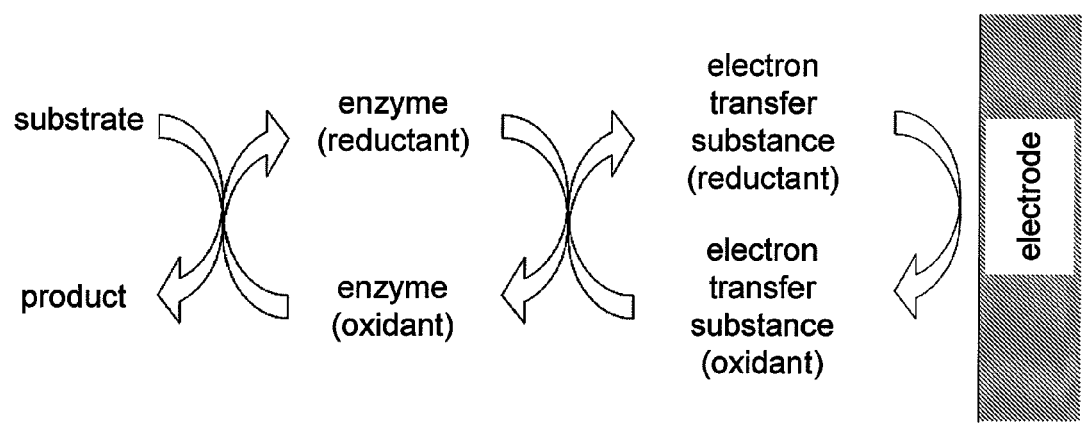
FIG. 3 is a diagram illustrating an example of an electrochemical reaction in a biosensor.

The work of the electron transfer substance will be described through reference to FIG. 3. FIG. 3 is a diagram illustrating the flow of a reaction in the active component 107 when an oxidase that oxidizes a substrate (target substance) is used.

As shown in FIG. 3, since the enzyme in the reagent layer 120 is an oxidase, it oxidizes the substrate and also accepts electrons from the substrate and changes from an oxidant into a reductant. An electron transfer substance that is an oxidant accepts electrons from an enzyme that has become a reductant, returning the enzyme to an oxidant, and itself becomes a reductant. An electron transfer substance that has become a reductant donates electrons to the electrodes 111a and 111b, and itself becomes an oxidant. In this way the electron transfer substance mediates the movement of electrons between the enzyme and the electrodes.

Examples of the characteristics demanded of an electron transfer substance are that electron movement between an enzyme and electrodes can be carried out smoothly, that it be possible to form an oxidant stably over an extended period in a reaction reagent, that the solubility be high, that the price be low, and so forth. In addition to these, another important characteristic demanded of an electron transfer substance is a low redox potential. This is because there are cases when latently reductive interference substances (chemical substances that can generate interference current in the presence of an electric field), such as acetaminophen, uric acid, ascorbic acid, or other such readily oxidized substances, are contained in the liquid sample used for measurement. If amperometric measurement is conducted in the presence of these interference substances, the interference substances are oxidized simultaneously with the oxidation of the reductive electron transfer substance on the electrodes, so an undesired signal may end up being measured. An electron transfer substance with a low redox potential is used to reduce the effect of these interference substances. This allows the electrode potential to be kept fairly low during measurement, and allows the rate to be slowed because the rate of potential is controlled in oxidation of the interference substances on the electrodes. However, an electron transfer substance with a low potential is often unstable, slow to dissolve, difficult to synthesize, and expensive. Examples of favorable electron transfer substances include metal complexes and other such inorganic electron transfer substances, and quinone derivatives and other such organic electron transfer substances.

In most cases, the electron movement rate between the enzyme and the electrodes will not be sufficiently high with an enzyme alone, and it will be difficult to obtain a signal with the strength required for measurement within a limited measurement time. In contrast, with this embodiment, an electron transfer substance is present along with an enzyme in the reagent layer 120, which allows an electrical signal to be obtained with measurable strength.

The reagent layer 120 may also contain other components besides the reaction reagent. A variety of substances that facilitate adhesion of the reagent layer 120 inside the recess 102, or improve storage stability of the reaction reagent, or increase reactivity between the reaction reagent and the target substance can be used as components other than the reaction reagent. A buffer is an example of such a component. These components preferably do not impede the dissolution of the reaction reagent into the liquid sample.

(1-5) Spacer 130 and Upper Cover 140

As shown in FIGS. 1 and 2, the spacer 130 is a member that provides a space between the upper cover 140 and the conductive layer 110.

More specifically, the spacer 130 is a plate-like member, which covers the entire conductive layer 110 except for the recess 102 and the two terminals 112 and 112b. The spacer 130 has a rectangular cut-out 131 that exposes from one short side of the spacer 130 to the recess 102. Because the spacer 130 has this cut-out 131, the liquid sample chamber 150 is formed, bounded by the conductive layer 110 and the upper cover 140.

Thus, the spacer 130 provides the side walls of the liquid sample chamber 150, and can delineate the length, width, height, etc., of the liquid sample chamber 150.

The liquid sample chamber 150 draws in the liquid sample by capillary action from an intake port 151 (an opening in the chamber) and holds the sample over the active component 107. The intake direction here is indicated by d1 in FIG. 1. The intake direction d1 is the direction facing from the intake port 151 toward the liquid sample chamber 150. In this embodiment, the intake direction d1 is parallel to the X direction, that is, to the lengthwise direction of the base plate 101.

As shown in FIGS. 1 and 2, the upper cover 140 is a member in the form of a rectangular plate, and has a hole that passes through from top to bottom. This hole functions as a vent port 152 that leads from the liquid sample chamber 150 to the outside. The vent port 152 is an exhaust hole for discharging gas inside the liquid sample chamber 150 to the outside of the liquid sample chamber when a liquid sample is drawn into the liquid sample chamber 150.

In other words, there are no particular restrictions on the position or shape of the intake port 151 and the vent port 152, as long as the lead from outside the liquid sample chamber 150 to the inside. However, the vent port 152 is preferably provided at a location away from the intake port 151, that is, deeper inside the liquid sample chamber 150 as viewed from the intake port 151. Disposing the intake port 151 in this way allows the liquid sample to move rapidly to the back part of the liquid sample chamber 150 from the intake port 151.

(1-6) Detailed Configuration of Recess 102

In general, it is difficult to adjust the intake of a liquid sample into the liquid sample chamber of the biosensor so that the rate is always constant. Particularly when the liquid sample is blood, the effects of the hematocrit value of the blood, the total cholesterol amount, the total protein amount, and so forth can produce a major difference in the viscosity of the liquid sample depending on who provided the blood, so there will also be a major difference in the intake rate. Furthermore, variance in the intake rate is affected by how skilled the user is at using the biosensor. With an unskilled user, there tends to be variance in the intake rate every time a measurement is made.

In recent years biosensors, and particularly blood glucose level sensors, have been rapidly becoming smaller and the measurement time shorter. As biosensors become more compact, the liquid sample intake port becomes smaller and harder to see for the user. Consequently, when the user applies a liquid sample to the biosensor, variance is even more likely to occur in the intake rate between measurements.

Also, in order to shorten the measurement time, reaction reagents with higher resolubility have often been used in recent years so that the reaction reagent will redissolve quickly when the liquid sample touches the reaction reagent. If a reaction reagent with higher resolubility is thus used, the reaction reagent that has redissolved in the liquid sample tends to be carried away from on the electrode in the liquid sample intake direction. Here, when the variance in the intake rate of the liquid sample increases, it drives up the variance in the concentration of the reaction reagent on the electrodes. As a result, measurement accuracy suffers and there is a decrease in reliability of the measurement result.

In contrast, with this embodiment, as shown in FIG. 2, the active component 107 is formed inside the recess 102. That is, the reagent layer 120 is disposed so as to cover the recess 102, which means that it is disposed at a depressed location in the first side 103 of the base plate 101. Consequently, the flow of the redissolved reaction reagent can be controlled with the biosensor 1. In other words, with the biosensor 1, the reaction reagent is less likely to be carried away in the intake direction d1 from on the electrodes 111a and 111b, and variance in the concentration of the reaction reagent on the electrodes 111a and 111b is kept low. As a result, good measurement accuracy can be maintained.

The structure of the recess 102 will be described in further detail.

As shown in FIGS. 1 and 2, the recess 102 is formed by having the thickness of the base plate 101 be less than that of the surrounding area. In other words, the portion corresponding to the rear side of the recess 102 does not protrude on the second side 104 of the base plate 101. Consequently, an advantage is that if the user's finger, a mounting component 201 (discussed below), or the like should touch the second side 104, the recess 102 is unlikely to deform, and the volume inside the recess 102 is unlikely to change. In this embodiment, the second side 104 has a flat shape, but the same advantage can be obtained even if the second side 104 is such that the portion corresponding to the rear side of the recess 102 is depressed more than the surrounding area.

As shown in FIG. 2, the recess 102 comprises a bottom face 108 and a side face 109. The bottom face 108 comprises the peaks 105 and valleys 106.

The "peaks" here are portions that have a peaked shape, that is a convex shape that tapers toward the distal end, while the "valleys" have a valley shape that is the inverse of the peaks, that is, a concave shape that narrows toward the bottom. The peaks and valleys may exhibit their peaked and valley shapes in either the Y direction or the X direction. That is, the peaked shape may be a ridge shape that extends continuously in one direction. The same applies to the valley shape.

There are no particular restrictions on the number and specific shape, etc., of the peaks 105 and valleys 106 provided inside the recess 102 of the biosensor 1, and may be suitably determined according to the size and shape of the recess 102, the composition of the reagent layer 120, the type of reaction reagent contained in the reagent layer 120, the type of target substance, the viscosity of the liquid sample, and other such characteristics.

To enhance the above-mentioned effect, the number of the peaks 105 and valleys 106 in the intake direction d1 is preferably at least one each, and more preferably at least 5 each, and even more preferably at least 10 each, and more preferably still at least 20 each. In other words, it is preferable if a plurality of peaks 105 and valleys 106 cross the intake direction d1 so as to collect the reaction reagent in the recess 102. If the peaks 105 and valleys 106 are disposed in this manner, then during liquid sample intake, the reaction reagent can be prevented from moving to a location away from the electrodes 111a and 111b.

Also, with the recess 102, the peaks 105 and valleys 106 can be, for example, in a dotted form, linear, square, or a curved shape, or these can be duplicated or combined. The word "duplicate" here means that the same shape is repeated a plurality of times, and "combine" means that different shapes are put together. That is, there are no particular restrictions on the pattern of the bottom face structure of the recess 102 in the X-Y planar direction. However, it is preferable if at least the peaks 105 or the valleys 106 are in a shape that crosses the intake direction d1. To put this another way, the peaks 105 or the valleys 106 or both are preferably in a shape that is not parallel to the intake direction d1.

From the standpoint of controlling the flow of the reaction reagent, the depth D1 of the apex of the peaks 105 is preferably at least 1 μm, and more preferably at least 5 μm, and even more preferably at least 10 μm. The depth D2 of the deepest part of the valleys 106 is preferably no more than 1000 μm, and more preferably no more than 300 μm, and even more preferably no more than 100 μm. More specifically, the depth of the recess 102 of the biosensor 1 is preferably at least 1 μm and no more than 1000 μm, and more preferably at least 5 μm and no more than 300 μm, and even more preferably at least 10 μm and no more than 100 μm.

From the standpoint of controlling the flow of the reaction reagent, the depth D1 is preferably at least 1% the height H1, and more preferably at least 5%, and even more preferably at least 10%. Similarly, the depth D2 is preferably no more than 300% the height H1, and more preferably no more than 200%, and even more preferably no more than 100%. More specifically, the depth of the bottom face 108 of the recess 102 is preferably 1 to 300% the height H1, and more preferably 5 to 200%, and even more preferably 10 to 100%.

As shown in FIG. 2, the depths D1 and D2 are, respectively, the distance in the Z direction between the lip 16 of the recess 102 and the apex of the peaks 105, and the distance in the Z direction between the lip 16 and the deepest part of the valleys 106.

Also, in this embodiment, the side face 109 of the recess 102 is not perpendicular to the X-Y plane in a cross section parallel to the Z direction. The purpose of this is to obtain the effect of pulling in the liquid sample along the side wall during liquid sample intake. Since having the side face 109 not be perpendicular to the X-Y plane makes it more likely that the liquid sample will be pulled in along the side face, there is a lower probability that bubbles will remain in the liquid sample chamber during liquid sample intake. Another effect of having the wall not be perpendicular to the X-Y plane is that since the liquid sample will readily be pulled in along the side face, the liquid sample can be drawn in more smoothly. Thus, the effect of having the liquid sample drawn in from the intake port 151 be readily pulled into the recess 102 is obtained by having the side face be non-perpendicular. In this embodiment, as shown in FIG. 2, the closer to the second side 104, the narrower is the recess 102 in the X-Y direction, and the effect is particularly good with this embodiment.

Also, in this embodiment, since the electrodes 111a and 111b are composed of a conductive layer of a uniform thickness, the shape of the bottom face 108 (the shape, depth, etc., of the peaks 105 and valleys 106), the shape of the side face 109, and all other categories discussed for the structure of the recess 102 also apply to the electrodes 111a and 111b in the recess 102.

All or part of the thickness T1 of either of the two electrodes 111a and 111b disposed in the recess 102 of the biosensor 1, or both electrodes, is preferably no more than 1000 μm, and more preferably no more than 15 μm, and even more preferably no more than 0.05 μm. It is particularly favorable for the thickness of the portion of the electrodes 111a and 111b that is disposed inside the recess 102 to be within this range.

Thus setting the thickness of the electrodes in the recess 102 to be thin results in the size and shape of the recess including the electrodes to approximate the size and shape of just the recess 102 of the base plate 101, in which the electrodes are not disposed. Consequently, the structure of the recess including the electrodes can be delineated accurately.

(1-7) Size, etc., of Recess 102

Figure 4A:
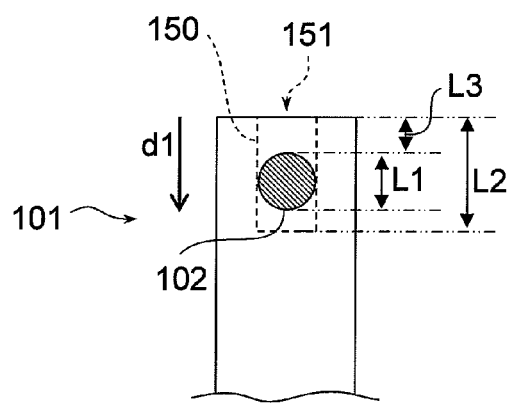
FIG. 4 consists of plan views of the position, etc., of the recess in the biosensor.
Figure 4A:
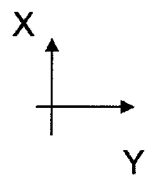
Figure 4B:
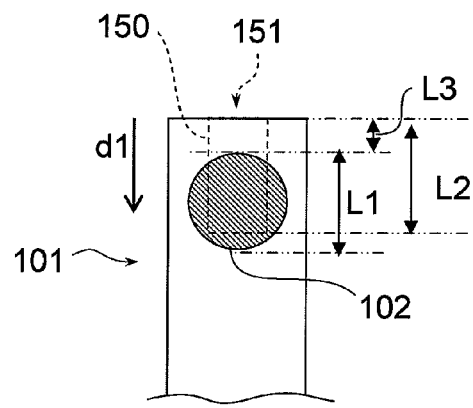
Figure 4B:
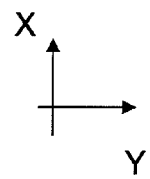

A particular example of the biosensor 1 will now be described through reference to FIGS. 4A and 4B, but the following constitution can be similarly applied to other biosensors as well. FIGS. 4A and 4B are plan views of the relationship between the position of the recess 102 in the biosensor 1 and the sizes of the recess 102 and the liquid sample chamber 150. For the sake of convenience, the liquid sample chamber 150 is indicated with a dotted line in the drawings.

Relationship Between Lengths L1 and L2

As shown in FIGS. 4A and 4B, we will let L1 be the maximum length of the recess 102 in the intake direction d1, and L2 be the maximum length of the liquid sample chamber 150 in the same direction d1. To further reduce the amount of liquid sample needed for detection, and to move the liquid sample quickly to the active component 107 by suction, the length L1 is preferably 0.1 to 99% the length L2, and more preferably 0.5 to 90%, and even more preferably 1 to 85%.

This holds true both when the entire recess 102 is exposed in the liquid sample chamber 150 in the intake direction d1 as in the example shown in FIG. 4A, and when part of the recess 102 is covered by the spacer 130 and not exposed in the liquid sample chamber 150 as in the example shown in FIG. 4B. In this embodiment, since the lip 16 of the recess 102 is circular, in both cases the length L1 is the same as the diameter of the lip 16.

Relationship Between Bottom Surface Area of Recess and Surface Area of Base Plate Exposed in Liquid Sample Chamber To further reduce the amount of liquid sample needed for detection, the bottom surface area of the recess 102 is preferably 0.1 to 99% the top surface area of the base plate 101 exposed in the liquid sample chamber 150, and more preferably 0.5 to 90%, and even more preferably 1 to 85%.

The "bottom surface area" of the recess 102 here is the surface area if we assume the bottom face 108 of the recess to be flat. That is, the phrase "bottom surface area" used here refers to the size of the bottom face 108 in just the X-Y plane, and does not factor in the presence of the peaks 105 and valleys 106.

Also, the "top surface area" of the base plate 101 exposed in the liquid sample chamber 150 is the surface area if we assume that the recess 102 is not present and the first side 103 of the base plate is flat. That is, in FIGS. 4A and 4B, the surface area of the entire rectangle indicated by the dotted lines as the liquid sample chamber 150 is the "top surface area." In this embodiment, since the liquid sample chamber 150 is a parallelepiped, the surface area of the liquid sample chamber 150 in the X-Y plane direction corresponds to this "top surface area."

Relationship Between Volume of Recess and Volume of Liquid Sample Chamber

To further reduce the amount of liquid sample needed for detection, the volume of the recess 102 is preferably 0.1 to 99% the volume of the liquid sample chamber 150, and more preferably 0.3 to 70%, and even more preferably 0.5 to 50%.

The volume of the recess 102 is the overall volume of the portion of the base plate that is depressed below the first side 103.

The volume of the liquid sample chamber 150 is the volume above the electrodes 111a and 111b or the first side 103 of the base plate, and includes the volume of the recess 102.

The volume of the liquid sample chamber 150 is calculated, for example, by totaling the volume of the portions bounded by the upper cover 140 and the spacer 130 and the electrodes 111*a* and 111*b* or the first side 103 of the base plate.

Volume of Recess

To further reduce the amount of liquid sample needed for detection, the volume of the recess 102 is preferably no more than 1 µL, and more preferably no more than 0.7 µL, and even more preferably no more than 0.5 µL. There are no particular restrictions on the lower limit to the volume of the recess 102, which is set by the relationship to the volume of the liquid sample chamber 150 as discussed above.

Position of Recess

To further reduce the amount of liquid sample needed for detection, and to move the liquid sample quickly to the active component 107 by suction, as shown in FIGS. 4A and 4B, the shortest distance L3 between one of the four sides of the base plate 101, and particularly the side on which the intake port 151 is provided, and the recess 102 is preferably no more than 5 mm, and more preferably no more than 3 mm, and even more preferably no more than 1.5 mm. More specifically, the distance from the intake port 151 to the recess 102 is preferably within this range.

(2) Biosensor Embodiment 2

Figure 5:
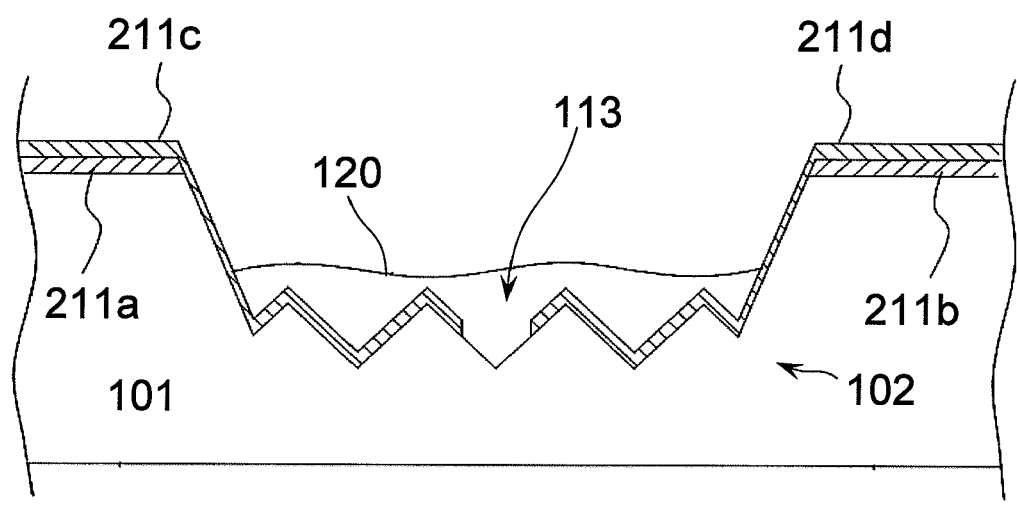
FIG. 5 is a cross section of another embodiment of the biosensor with electrodes of which shape are different from FIG. 2.

The biosensor 1 may comprise electrodes 211*a*, 211*b*, 211*c* and 211*d* shown in FIG. 5 instead of the electrodes 111*a* and 111*b*. FIG. 5 is a cross section of the base plate, electrodes, and reagent layer in this embodiment. Those members, etc., that have already been described are numbered the same in the drawings and may not be described again.

As shown in FIG. 5, in this embodiment, inorganic electrodes 211*a* and 211*b* composed of an inorganic conductive substance are provided on the base plate 101, and organic electrodes 211*c* and 211*d* composed of an organic conductive substance are provided over the inorganic electrodes.

In this embodiment, the inorganic electrodes 211*a* and 211*b* are not provided inside the recess 102, and only the organic electrodes 211*c* and 211*d* are provided, but this is not the only option, and the inorganic electrodes 211*a* and 211*b* and the organic electrodes 211*c* and 211*d* may be stacked within the recess 102 as well.

The constitution discussed in section (1) above is applicable to this embodiment, except that the electrodes are stacked.

(3) Biosensor Embodiment 3

Figure 6:
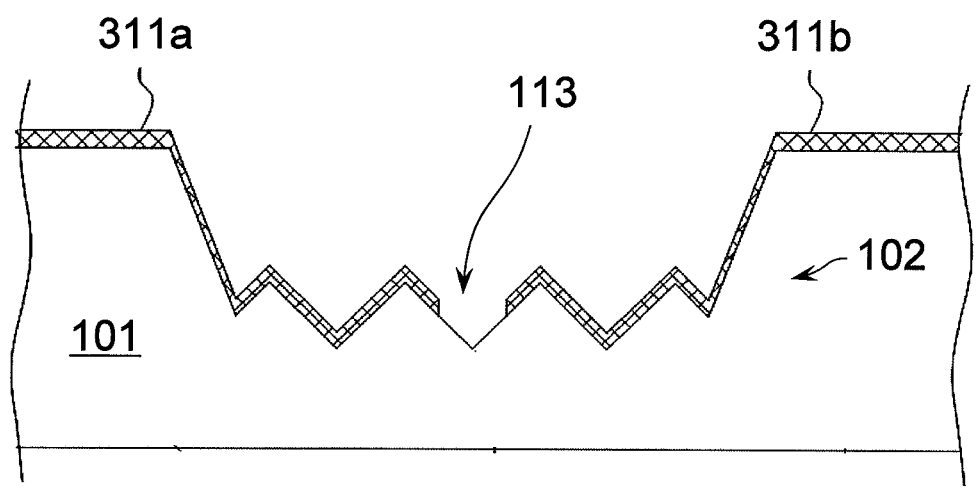
FIG. 6 is a cross section of another embodiment of the electrode.

The biosensor 1 may comprise the electrodes 311*a* and 311*b* shown in FIG. 6 instead of the electrodes 111*a* and 111*b*. FIG. 6 is a cross section of the base plate and electrodes in this embodiment. Other than the constitution of the electrodes, the constitution discussed in section (1) above can be used. Those members, etc., that have already been described are numbered the same in the drawings and may not be described again.

As shown in FIG. 6, in this embodiment, the electrodes 311*a* and 311*b* are conductive layers containing an organic conductive substance such as carbon or a conductive polymer, and include a reaction reagent (containing an enzyme and an electron transfer substance) to perform the desired measurement. The electrodes 311*a* and 311*b* may be formed by printing just as with the electrodes of the biosensor 1, or they may be formed by coating the base plate 101 with a conductive material and a reaction reagent, and then forming non-conductive tracks 113 by laser ablation or the like. When a reaction reagent component is thus contained in a conductive material, in other words, the electrodes are made into reaction reagent-containing electrodes, the number of manufacturing steps can be reduced, and less expensive manufacture is possible.

The constitution discussed in section (1) above is applicable to this embodiment, except that the electrodes contain a reaction reagent.

(4) Biosensor Embodiment 4

Figure 7:
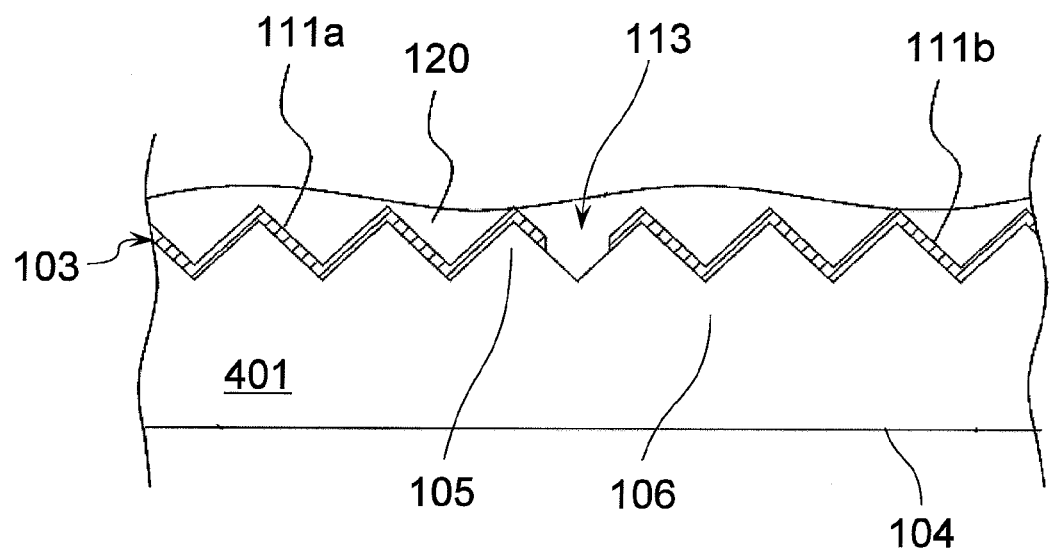
FIG. 7 is a cross section of another embodiment of the biosensor base plate.

With the biosensor 1, the base plate 401 shown in FIG. 7 may be used in place of the base plate 101. FIG. 7 is a cross section of the base plate and electrodes pertaining to this embodiment. Other than the constitution of the base plate, the constitution described in section (1) can be used. Those members, etc., that have already been described are numbered the same in the drawings and may not be described again.

As shown in FIG. 7, the whole shape of the first side 103 of the base plate 401 is roughly indented. In particular, the peaks 105 and valleys 106 are alternately disposed over all the first side 103 of the base plate 401. The electrodes 111*a* and 111*b* are disposed on a part of the first side 103 so as to conform to concavo-convex shape of the first side 103. The reagent layer 120 is disposed on the electrodes 111*a* and 111*b*.

With the base plate 401, the plurality of valleys 106 work together to provide the same function as the recess 102 shown in FIG. 2 and elsewhere. That is, a biosensor in which the base plate 401 of this embodiment is employed is also substantially constituted so that the reagent layer 120 is disposed so as to cover the bottom face of a recess having the electrodes 111*a* and 111*b*, and will therefore be readily understood to be an embodiment of the present invention.

Also, for the parts of the constitution that are not specifically mentioned in this embodiment, the constitution described in section (1) is applied.

(5) Biosensor Embodiment 5

Figure 8A:
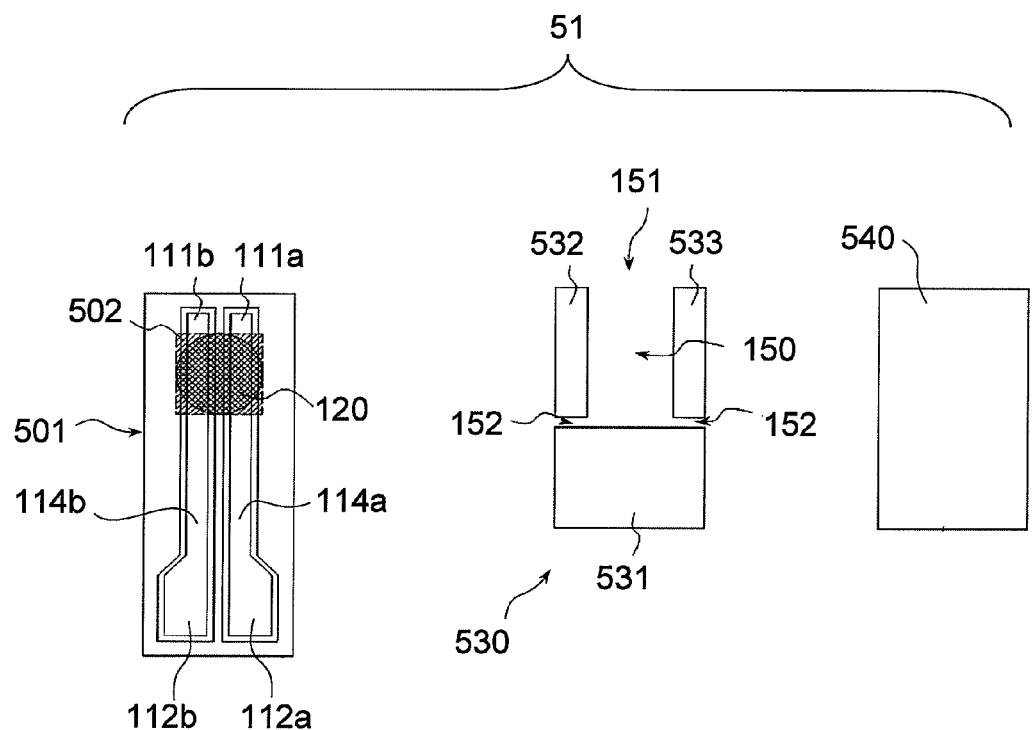
FIGS. 8A and 8B are exploded plan views of another embodiment of the biosensor.

Yet another embodiment of a biosensor will be described through reference to FIG. 8A. FIG. 8A is a diagram illustrating the constitution of the biosensor 51 in this embodiment, and is a plan view of a base plate (including electrodes and a reagent layer), a spacer, and an upper cover. Those members with the same function as members which have already been described are numbered the same in the drawings and may not be described again.

As shown in FIG. 8A, with the biosensor in this embodiment, a base plate 501 is equipped with a rectangular recess 502 in place of the recess 102. The two electrodes 111*a* and 111*b* have a depressed shape that conforms to this recess 502. The reagent layer 120 is disposed in a circular shape that inscribes the rectangular shape of the recess 502. Thus, there is no need for the reagent layer to cover the entire recess.

A spacer 530 is mounted on the surface of the base plate 501. The spacer 530 is divided into three rectangular spacers, namely, a first spacer 531, a second spacer 532, and a third spacer 533.

The first spacer 531 is disposed so that its four sides are parallel to the respective four sides of the base plate 501, and so as to cover the conductive portion between the recess 502 and the terminals 112*a* and 112*b*.

The second spacer 532 and the third spacer 533 are disposed flanking the recess 502 in the short side direction of the base plate 501. That is, the second spacer 532 and the third spacer 533 are disposed so that their lengthwise direction is parallel to the lengthwise direction of the base plate 501, and so that the recess 502 is surrounded on three sides by the first spacer 531, the second spacer 532, and the third spacer 533. The second spacer 532 and the third spacer 533 are each disposed with a gap between them and the first spacer 531.

Disposing the spacer 530 in this way results in a state in which the terminals 112a and 112b and the recess 502 are exposed from the spacer 530.

An upper cover 540 is further disposed over the spacer 530. A gap is formed by the spacer 530 between the upper cover 540 and the base plate 501. The liquid sample chamber 150 is thus formed, bounded by the base plate 501, the spacer 530, and the upper cover 540. The gap between the second spacer 532 and the third spacer 533 also functions as the intake port 151. A vent port is not provided as a through-hole to the upper cover 540, and the gap between the second spacer 532 and the first spacer 531, and the gap between the third spacer 533 and the first spacer 531 function as the above-mentioned vent port 152.

With a biosensor such as this, just as with the biosensor 1, the intake direction of the liquid sample is the direction facing the terminals 112a and 112b from the electrodes 111a and 111b, that is, it is parallel to the lengthwise direction of the biosensor.

(6) Biosensor Embodiment 6

Figure 8B:
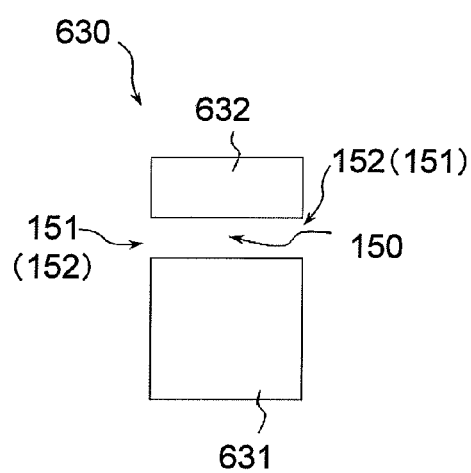

With the biosensor described in section (5) above, the spacer 630 shown in FIG. 8B may be used in place of the spacer 530.

As shown in FIG. 8B, the spacer 630 is composed of a first spacer 631 and a second spacer 632. The first spacer 631 is disposed between the terminals 112a and 112b and the recess 502 shown in FIG. 8A, while the second spacer 632 is disposed so as to provide a gap parallel to the short side direction of the base plate 501 between itself and the first spacer 631. The recess 502 is exposed in this gap.

The result of providing this spacer 630 is that the liquid sample chamber 150 has a shape that perpendicularly crosses the base plate 501 in its lengthwise direction, from one long side of the base plate 501 to the other long side, over the recess 502. With this embodiment, the liquid sample chamber 150 has two ends (openings) on the long sides of the base plate 501. Both these two openings can function as the intake port 151 through which the liquid sample is drawn into the liquid sample chamber 150. Regardless of which opening is used for intake, the intake direction of the liquid sample is perpendicular to the lengthwise direction of the biosensor. Also, of the two openings of the liquid sample chamber 150, when one functions as the intake port 151, the other functions as the vent port 152, and vice versa.

When there are thus intake ports at two locations, the recess 502 is preferably such that of the four sides of the base plate 501, the distance from either of the two sides on which the intake ports are disposed is within the same range as the above-mentioned distance L3.

(7) Biosensor Embodiment 7

Figure 9A:
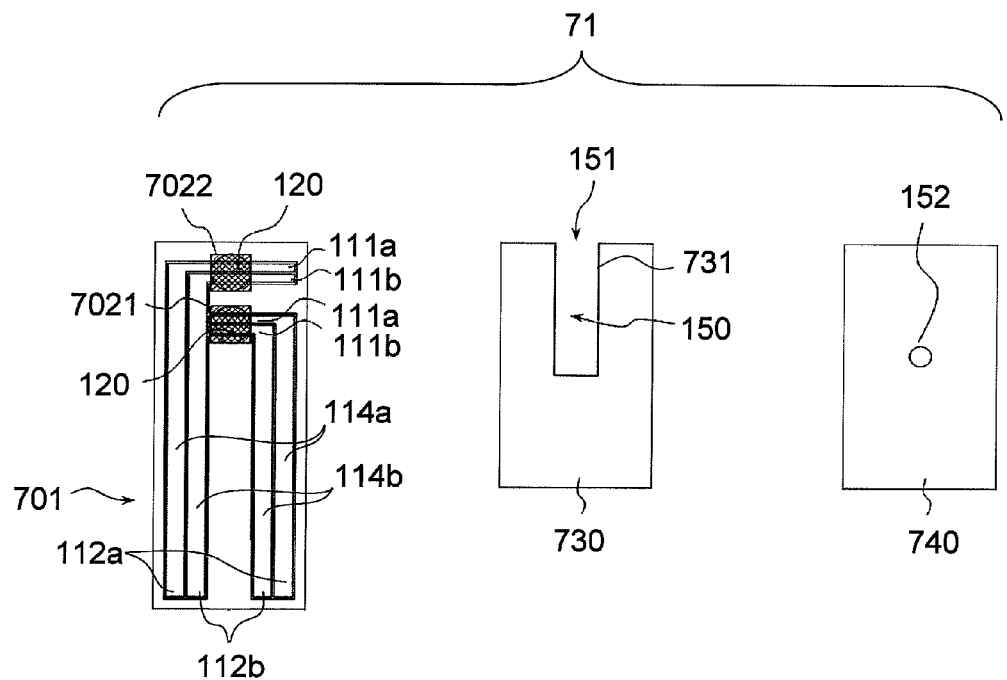
FIGS. 9A to 9C are exploded plan views of another embodiment of the biosensor.

Yet another embodiment of a biosensor will be described through reference to FIG. 9A. FIG. 9A is a diagram illustrating the constitution of a biosensor 71 in this embodiment, and is a plan view of a base plate (including electrodes and a reagent layer), a spacer, and an upper cover. Those members with the same function as members which have already been described are numbered the same in the drawings and may not be described again.

As shown in FIG. 9A, the biosensor may comprise a plurality of recesses in which a reagent layer and electrodes are disposed. More specifically, the base plate 701 in this embodiment comprises two recesses 7021 and 7022, and the reagent layer 120 and the two electrodes 111a and 111b are disposed in each of these recesses. The electrodes 111a and 111b and the terminals 112a and 112b are connected to each other, respectively. The recesses 7021 and 7022 are disposed in that order from the side closest to the terminals 112a and 112b in the lengthwise direction of the base plate 701.

A spacer 730 has a single continuous cut-out 731 so as to expose the two recesses 7021 and 7022. Also, the spacer 730 has a shape that exposes the terminals 112a and 112b. This spacer 730 forms the liquid sample chamber 150 inside the cut-out 731 and between an upper cover 740 and the base plate 701. The end of the cut-out 731 functions as the intake port 151.

The same type of member as the above-mentioned upper cover 140 can be used as the upper cover 740. That is, the upper cover 740 is a member in the form of a rectangular plate, and has at least one vent port 152 that is a through-hole that leads to the liquid sample chamber 150.

Thus, with the biosensor 71, two reaction components (the electrodes 111a and 111b and the reagent layer 120) are disposed in a single liquid sample chamber 150. Consequently, two sensing operations can be performed with the biosensor 71. Also, three or more reaction components can be provided with the same constitution.

The shape and formation method of the two recesses 7021 and 7022 may be mutually the same or different.

The reaction reagent inside the reagent layer 120 disposed in the recesses 7021 and 7022 may have the same composition to detect the same target substance, or may have different compositions to detect the same target substance, or may have different compositions to detect different target substances.

Providing a plurality of reaction components for the same target substance allows measurement of the same target substance to be performed a plurality of times with a single biosensor, so reliability of the measurement accuracy can be improved. Also, providing a plurality of reaction components that react with different target substances allows a plurality of target substances to be detected and measured at the same time with a single biosensor, which is more convenient for the user.

Furthermore, the user can select the required measurement categories according to the situation at hand, from among the available measurement categories. Although not depicted in the drawings, if there are a plurality of liquid sample chambers, the various liquid sample chambers may be disposed in the same plane of the base plate that constitutes the biosensor, or may be disposed in different planes.

Also, the size and so forth of the various components discussed in section (1-7) above can be applied favorably with a biosensor comprising a plurality of recesses on a single base plate as in this embodiment.

Specifically, in this embodiment, in the relationship between the lengths L1 and L2 described through reference to FIGS. 4A and 4B, the length L1 can be substituted with the length L11 of the recess 7021 and the length L12 of the recess 7022. That is, in the relationship with the length L2, it is preferable if the lengths L11 and L12 are each within the same range as that discussed above for the length L1. Similarly, when there are three or more recesses, the length of each recess exposed in the liquid sample chamber is preferably within the above-mentioned range with respect to the length of the liquid sample chamber.

Also, in this embodiment, in the relationship between the bottom surface area of the recess 102 and the surface area of the base plate 101 exposed in the liquid sample chamber 150, the bottom surface area of the recess 102 can be substituted with the total bottom surface area obtained by summing the bottom surface areas of the two recesses 7021 and 7022. Similarly, if there are three or more recesses, the sum of the bottom surface areas of all the recesses exposed in a single liquid sample chamber is preferably within the above-mentioned range with respect to the surface area of the base plate exposed in this liquid sample chamber.

Also, in this embodiment, in the relationship between the volume of the recess 102 and the volume of the liquid sample chamber 150, the volume of the recess 102 can be substituted with the total volume obtained by summing the volumes of the two recesses 7021 and 7022. Similarly, when there are three or more recesses, the sum of the volumes of all the recesses exposed in a single liquid sample chamber is preferably within the above-mentioned range with respect to the volume of a single liquid sample chamber.

The combined volume of the recesses 7021 and 7022 is preferably 1 μL or less, and more preferably 0.7 μL or less, and even more preferably 0.5 μL or less. Similarly, when there are three or more recesses, the sum of the volumes of the plurality of recesses is preferably within this range.

Also, the distance L3 described through reference to FIGS. 4A and 4B is applied to the recess 7022 that is closer to the intake port 151. That is, L3 is the distance from the side of the base plate 701 on which the intake port 151 is provided, to the recess 7022. The same applies when three or more recesses are provided.

(8) Biosensor Embodiment 8

Figures 9B, 9C:
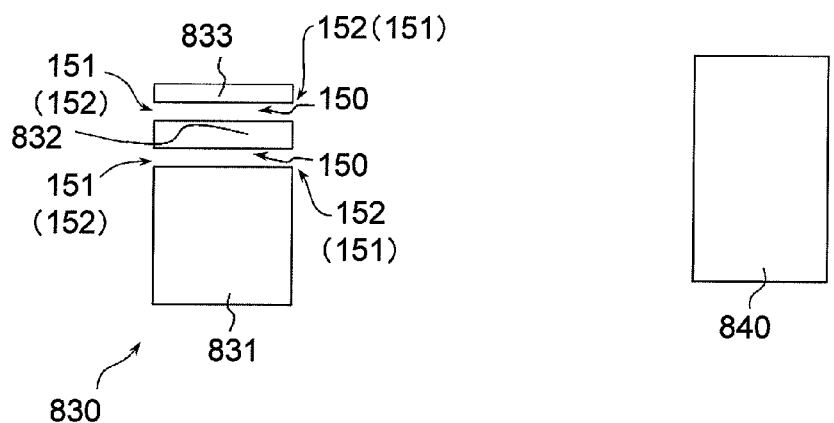
Figure 10:
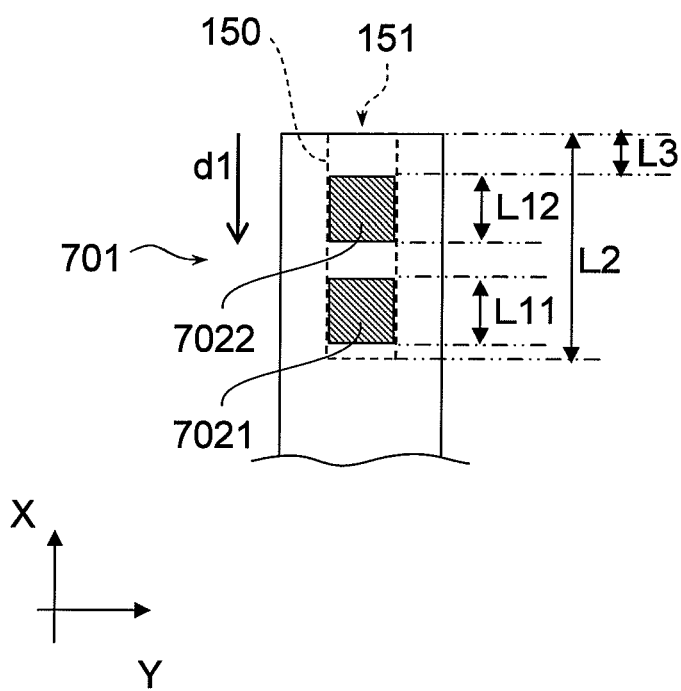
FIG. 10 is a plan view of the position, etc., of the recess in the biosensor shown in FIG. 9A.

With the biosensor in section (7) above, the spacer 830 shown in FIG. 9B and the upper cover 840 shown in FIG. 9C can be used in place of the spacer 730 and the upper cover 740, respectively.

As shown in FIG. 9B, the spacer 830 is composed of three rectangular spacers, namely, a first spacer 831, a second spacer 832, and a third spacer 833. The first spacer 831 is disposed between the terminals 112a and 112b and the recess 7021, the second spacer 832 is disposed between the recess 7021 and the recess 7022, and the third spacer 833 is disposed at a location farther away from the terminals 112a and 112b than the recess 7022. The spacer 831, 832 and 833 are disposed with the gaps between each other.

As shown in FIG. 9C, the upper cover 840 is rectangular in shape, and is disposed so as to expose the terminals 112a and 112b and cover the spacer 830.

The two gaps between the spacers 831 to 833 form two liquid sample chambers 150 that are bounded by the upper cover 840 and the base plate 701. The two liquid sample chambers 150 pass over the two recesses 7021 and 7022, respectively, and have a shape that perpendicularly crosses the base plate 701 in its lengthwise direction, from one long side of the rectangular base plate 701 to the other long side.

With this embodiment, the liquid sample chambers 150 each have two ends (openings) on the long sides of the base plate 701. The liquid sample can be drawn into the liquid sample chamber 150 from either of these two openings. Regardless of which opening is used for intake, the intake direction of the liquid sample is perpendicular to the lengthwise direction of the biosensor.

Also, with each liquid sample chamber 150, when one of the two openings functions as the intake port 151, the other functions as the vent port 152, and vice versa.

(9) Other Embodiments 9-1

In the embodiments given above, the recess (the recess 102, etc.) provided on the base plate had in its interior the peaks 105 and valleys 106, but the base plate is not limited to this shape, as long as it is equipped with a recess and the portion corresponding to the rear side of this recess does not stick out from the surrounding area.

9-2

The shape of the above-mentioned recess is not limited to a shape comprising the peaks 105 and valleys 106 as in the above embodiments, and all or part of the bottom face may be flat.

9-3

The above-mentioned recess preferably has a convex or concave structure on its bottom face. A "convex structure" is a shape which protrudes in the thickness direction of the base plate, while a "concave structure" is a shape which is depressed in the thickness direction of the base plate. An advantage to thus providing a convex or concave structure to the recess is that it is easier to control the flow of reaction reagent during liquid sample intake. That is, the peaks 105 and valleys 106 in the embodiments given above are an example of a convex structure and a concave structure.

Specifically, with the recess 102 in FIG. 2, the peaks 105 can be replaced with a convex structure other than a peaked shape, and the valleys 106 can be replaced with a concave structure other than a valley shape. Nevertheless, the effect is better when the convex structure and concave structure are the above-mentioned peaks and valleys. The effect is particularly good when a repeating pattern of peaks and valleys is formed in the recess as in the embodiment shown in FIG. 2.

9-4

In section (1) above, preferred ranges were given for the number and depth of the peaks 105 and valleys 106, and these ranges also apply to convex and concave structures other than peaked and valley shapes.

9-5

In all of the above embodiments, the electrodes 111a and 111b, the conductive tracks 114a and 114b, and the terminals 112a and 112b do not all have to be formed on the same base plate, and may be formed on different base plates (a first plate and a second plate).

Figure 28:
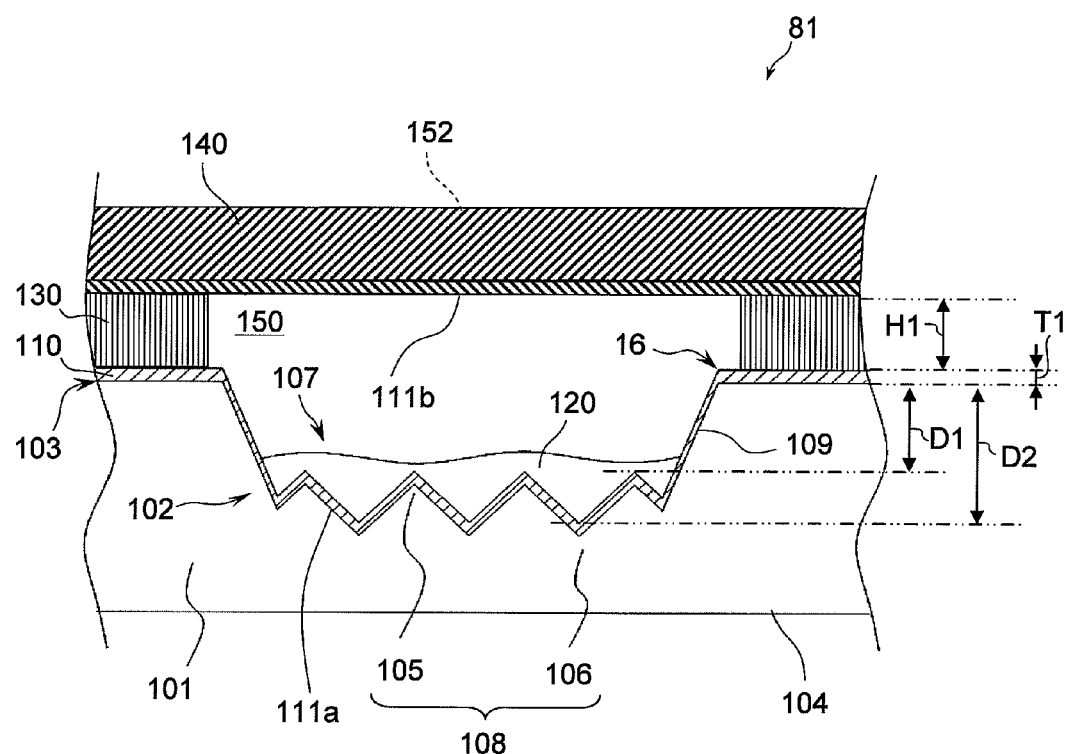
FIG. 28 is a cross section of the biosensor pertaining to another embodiment.
Figure 28:
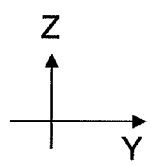

This constitution will be described through reference to FIG. 28. In FIG. 28, those members and positions that have already been described are numbered the same in the drawings and will not be described again.

As shown in FIG. 28, with a biosensor 81, the electrode 111a and the reagent layer 120 are disposed inside the recess 102 of the base plate 101, and the electrode 111b is disposed on the lower face of the upper cover 140 (that is, the face opposite the base plate 101). Specifically, the biosensor 81 comprises the base plate 101 as a first plate, and the upper cover 140 as a second plate.

Either of the electrodes 111a and 111b may function as a working electrode, or may function as a counter electrode.

The constitution of the various components, such as the upper cover 140, the spacer 130, and the electrodes 111a and 111b, can be changed as discussed in the embodiments above. Specifically, the number of electrodes is not limited to two, and can be changed.

9-6

Biosensors obtained by combining the constitutions in sections (1) to (8) above, as well as biosensors obtained by combining the constitutions in sections (9-1) to (9-5), are also encompassed by embodiments of the present invention. For instance, with the biosensors 51 and 71 shown in FIGS. 8A and 9A, the structures shown in FIGS. 5 to 7 can be applied to the recesses 502, 7021, and 7022.

9-7

The biosensor may also have a structure as follows.

(1) The biosensor may be one that detects the presence of a target substance contained in a liquid sample, comprising an insulating base plate having a recess formed in a portion that is thinner than the surrounding part, a working electrode and a counter electrode, at least one of which is disposed in the recess, and a reaction reagent that is disposed in the recess and reacts with a specific substance in the liquid sample.

With this biosensor, the base plate has a recess, and the reaction reagent is disposed in this recess, so the reaction reagent is effectively prevented from flowing out from on the base plate. Consequently, even if the solubility of the reaction reagent is raised, it will still be possible to detect the target substance, and detection will take less time. Thus shortening the time it takes for detection makes this biosensor more convenient for the user.

Also, since the recess is formed by adjusting the thickness of part of the insulating base plate, there is no need for another member besides the base plate to form the recess. Thus, there is no or less increase in the number of members, nor an increase in the manufacturing cost.

Furthermore, since the recess is formed by making part of the base plate thinner, there is no bump or recess on the rear side of the base plate. Thus, if the rear side of the base plate should be touched by the user, etc., it is unlikely that the volume of the recess will change, so good measurement accuracy can be achieved.

(2) With the biosensor in (1) above, the recess may comprise a concave structure that is depressed in the thickness direction of the base plate, or a convex structure that sticks out in the thickness direction of the base plate, or a combination of the two.

Because this biosensor comprises a concave structure and/or a convex structure, a recess that prevents the flow of the reaction reagent can be formed easily.

(3) With the biosensor in (2) above, the concave structure may include a valley shape that narrows toward the bottom.

(4) With the biosensor of (2) or (3) above, the convex structure may include a peaked shape that narrows toward the distal end.

Since the concave structure and the convex structure are formed so as to include these shapes, a recess that prevents the flow of the reaction reagent can be formed easily.

The shape of the concave structure or the convex structure can be as follows.

(5) For instance, with the biosensor pertaining to any of (2) to (4) above, the shape of the concave structure or the convex structure in the planar direction of the base plate may be in a dotted form, linear, square, or a curved shape, or two or more of these shapes may be combined.

(6) With the biosensor pertaining to any of (2) to (4) above, the outer edge of the recess may be circular, and a concave structure and a convex structure may be provided alternately on the bottom face of the recess so as to scribe a circular shape concentric with the outer edge.

(7) With the biosensor pertaining to any of (2) to (4) above, the outer edge of the recess may be circular, and a concave structure may be provided in a grid pattern on the bottom face of the recess, and the portions surrounded by the concave structure may serve as the convex structures.

(8) With the biosensor pertaining to any of (2) to (4) above, the outer edge of the recess may be rectangular, and the concave structure may be provided in a grid pattern on the bottom face of the recess, and the portions surrounded by the concave structure may serve as the convex structures.

(9) With the biosensor pertaining to any of (1) to (8) above, the biosensor may further comprise a liquid sample chamber to hold the liquid sample, above the recess in the thickness direction of the base plate.

If the biosensor thus has a liquid sample chamber, it is possible to reduce the amount of liquid sample required for detection.

(10) With the biosensor pertaining to (9) above, the biosensor may further comprise an intake port to draw a liquid sample by capillary action from the outside into the liquid sample chamber.

If the biosensor thus comprises an intake port, it will be possible to supply the liquid sample quickly to the liquid sample chamber by capillary action.

(11) With the biosensor pertaining to (9) or (10) above, the biosensor may further comprise a vent port to discharge air from inside the liquid sample chamber to the outside.

Thus providing a vent port to the biosensor allows the inside of the liquid sample chamber to be quickly filled with a liquid sample.

(12) With the biosensor pertaining to any of (1) to (11) above, at least part of the side face of the recess may be non-perpendicular to the planar direction of the base plate. The "the planar direction of the base plate" may be "the direction facing the liquid sample chamber from the intake port."

With this biosensor, the liquid sample supplied through the intake port is able to move quickly to the recess.

(13) With the biosensor pertaining to any of (1) to (12) above, the biosensor may further comprise a spacer disposed on the base plate so that at least part of the recess is exposed, and an upper cover may be disposed over the spacer so as to cover the recess exposed from the spacer.

(14) With the biosensor pertaining to any of (1) to (13) above, the biosensor may further comprise terminals to electrically connect the working electrode and counter electrode with a detection device to detect a target substance from the current value of the biosensor.

(15) With the biosensor pertaining to any of (1) to (14) above, the reaction reagent may be disposed on the working electrode and the counter electrode.

(16) With the biosensor pertaining to any of (1) to (15) above, the working electrode and/or the counter electrode may contain an electroconductive substance.

(17) With the biosensor pertaining to (16) above, the electroconductive substance may include inorganic electroconductive substances.

(18) With the biosensor pertaining to (17) above, the working electrode and/or the counter electrode may contain palladium.

(19) With the biosensor pertaining to any of (16) to (18) above, the electroconductive substance may include organic electroconductive substances.

(20) With the biosensor pertaining to (19) above, the working electrode and/or the counter electrode may contain an electroconductive polymer.

(21) With the biosensor pertaining to any of (1) to (20) above, an enzyme may be disposed in the recess.

(22) With the biosensor pertaining to (21) above, oxidase or dehydrogenase may be disposed in the recess. These enzymes are favorable as the reaction reagent.

(23) With the biosensor pertaining to (22) above, oxidase or dehydrogenase may be disposed in the recess. A substrate of the oxidase and the dehydrogenase may be glucose. These enzymes are favorable as the reaction reagent.

(24) With the biosensor pertaining to any of (1) to (23) above, an electron transfer substance may be disposed in the recess. An electron transfer substance can transfer signals generated by electrochemical reaction in the biosensor.

(25) With the biosensor pertaining to (24) above, hexacyano iron(III) potassium may be disposed in the recess. Hexacyano iron(III) potassium is favorable as an electron transfer substance.

(26) With the biosensor pertaining to any of (1) to (25) above, the reaction reagent may be in a dry state. The storage stability of the reaction reagent is better with this biosensor.

(27) With the biosensor pertaining to any of (1) to (26) above, the working electrode and counter electrode may be electrodes that measure the hemocyte component in a liquid sample.

(28) With the biosensor pertaining to any of (1) to (26) above, the working electrode and counter electrode may be electrodes that measure easily oxidizable substances in a liquid sample.

(29) With the biosensor pertaining to any of (1) to (26) above, the working electrode and a counter electrode are electrodes that detect intake of a liquid sample.

(30) With the biosensor pertaining to any of (1) to (29) above, the biosensor comprises a first plate that is insulating and has the recess, and a second plate that is insulating and is disposed opposite the first plate, wherein the reaction reagent and one electrode from among the working electrode and the counter electrode are disposed in the recess on the first plate, and the other electrode from among the working electrode and the counter electrode is disposed on the second plate.

9-8

The method that comprises forming a recess by reducing the thickness of an insulating base plate, disposing a working electrode and/or a counter electrode in the recess, disposing a reaction reagent that reacts with a target substance in the recess, disposing a spacer on the base plate so as to expose at least part of the recess, and a disposing an upper cover over the spacer so as to cover the recess exposed from the spacer is preferably used as the method of producing these biosensors.

9-9

These biosensors can be used favorably in a detection system comprising a biosensor and a detection device to detect a target substance in a liquid sample from the current between the working electrode and the counter electrode of the biosensor.

Since this detection system includes one of the above-mentioned biosensors, the detection time can be shortened and user convenience can be enhanced. Also, there is no or less increase in the number of members, so there is no increase in manufacturing cost, and there is little change in the volume of the recess, so good measurement accuracy can be attained.

9-10

With the technology discussed in this Specification, a biosensor can be provided that is easy for a user to use, keeps increases in manufacturing cost down, and has good detection accuracy.

As discussed above, increasing user convenience and measurement accuracy have been emphasized in the technological development of biosensors to measure blood glucose levels in recent years.

Shortening the measurement time is considered particularly important in terms of ease of use. However, if the solubility of the reaction reagent is increased in order to shorten the measurement time, there is the risk that the reaction reagent will be carried away in the intake direction when the liquid sample is drawn into the liquid sample intake port, which would lower measurement accuracy.

Fixing the reaction reagent to an electrode, adding a polymer compound to the reaction reagent, and so forth have been attempted up to now as methods for keeping the reaction reagent on the electrode surface. These methods, however, require sophisticated manufacturing technology, and drive up the manufacturing cost. In addition, since the resolubility of a reaction reagent such as this is decreased by the liquid sample, the diffusion rate is lower. Since the reaction efficiency in the measurement environment is what determines the rate of diffusion, a lower diffusion rate decreases reaction efficiency, so the measurement time cannot be shortened. Furthermore, fixing the reaction reagent to the electrode surface or adding a polymer compound to the reaction reagent may decrease the storage stability of the biosensor.

Also, with a biosensor in which a reaction reagent holding layer is provided by stacking a base plate in which a cut-out is formed over a bottom plate, the number of parts needed for manufacturing a biosensor increases, and greater machining precision is required for the various members. As a result, the manufacturing process becomes more complicated, and manufacturing efficiency drops or costs rise.

Also, as a method for specifying the position of a reaction reagent and the reaction reagent distribution, a method has been attempted in which an electrode array is formed by forming conductive tracks in the area where the reaction reagent is disposed on the base plate, and forming a recess near this electrode array. With this method, however, although an increase in the reaction reagent disposition accuracy can be expected, the fluidity of the reaction reagent during liquid sample intake cannot be controlled.

Meanwhile, a method has been reported in which a groove is formed by embossing, without reducing the thickness of the base plate. With this method, the rear side of the base plate with respect to the grooves is worked into a shape that protrudes in a peaked form. Since this portion is directly touched by the user in mounting the biosensor to the measurement device, this shape clearly does not feel good to the user. Also, when touched by the user, or in transport, there is the risk that the portion protruding in a peaked shape will be deformed. If this portion is deformed, the groove shape and volume will change, so this has a major adverse effect on measurement accuracy. Furthermore, to perform embossing, it is predicted that the material will have to be selected very carefully. Accordingly, this technique cannot adequately satisfy the need for better measurement accuracy and convenience.

Thus, it is difficult to satisfy all three requirements of being easy to use by a user (and particularly taking less time to detect the target substance), keeping increases in manufacturing cost low, and good detection accuracy, and these three seem to be mutually exclusive. In the development of biosensors up to now, no one has directly attacked this problem, nor has any solution been proposed.

In contrast, the technology discussed in this Specification makes it possible to provide a biosensor with which all three of the above requirements can be met, and a method of producing this biosensor and a detection system equipped with the same.

B. Method of Producing Biosensor

The method of producing the biosensor 1 shown in FIGS. 1 and 2 will now be described. The following manufacturing method can be used to manufacture the biosensors pertaining to the various embodiments given above. The following manufacturing method is not intended to limit the constitution of the biosensor.

(1) Production of Base Plate

There are no particular restrictions on the method of producing the base plate 101 including the recess 102, as long as it is a method with which the recess 102 can be formed without protruding from the second side 104 and without adding any other members.

For instance, the recess 102 may be formed by working a flat insulating board, or the recess 102 may be formed by casting a liquid insulating material into a mold, and solidifying this insulating material in the casting mold.

Specific examples of methods for forming the recess 102 include laser ablation, stamping, anisotropic etching, cutting with a blade, and molding, and combinations of these can also be used. The type of laser used for laser ablation can be excimer, YAG, carbon dioxide, etc.

The material that constitutes the base plate 101 has already been discussed.

(2) Formation of Electrodes

The method for providing the electrodes 111a and 111b, the terminals 112a and 112b, and other conductive portions on the base plate 101 can be vapor deposition such as sputtering, or printing, dipping, coating, bonding, or the like can be used, and these techniques can also be combined. More specifically, the electrodes, terminals, and so forth may be formed by applying a conductive substance substantially uniformly over the base plate 101 by vapor deposition, coating, or the like, and then removing the conductive substance by laser ablation or the like to form the non-conductive tracks 113. The electrodes and terminals can also be formed by providing a conductive substance over the base plate 101 in a pattern that matches the shape of the electrodes, terminals, and so forth ahead of time.

The material constituting the electrodes, terminals, etc., has already been discussed.

The surface resistivity of the electrodes can be adjusted by varying the electrode formation conditions.

For example, Denatron P-502S, which is a specific example of an organic conductive substance, is in the form of a liquid with a viscosity of less than 30 mPa·s at 25° C. A polymer film with a thickness of 0.2 µm can be formed by using polyethylene terephthalate (Lumirror T60, marketed by Toray) as the base plate 101, coating the base plate 101 with a solution of liquid Denatron P-502S diluted 1.5 times in a coating thickness of 9 µm, and then drying for 1 minute at 100° C. This polymer film becomes an electrode having a surface resistivity of 1 MΩ/square.

(3) Formation of Reagent Layer

The reagent layer 120 can be produced, for example, by dissolving or dispersing a reaction reagent (including an enzyme and an electron transfer substance) and other components in a solvent, applying the resulting reaction solution over the electrodes 111a and 111b inside the recess 102, and drying this. Examples of how the reaction solution is applied inside the recess 102 include printing, coating, and dipping, and combinations of these can also be used.

(4) Disposition of Spacer and Upper Cover

The spacer 130 is fixed over the base plate 101 so as to expose at least part of the recess 102 of the base plate produced in section (1) above, and the upper cover 140 is fixed over the spacer 130 so as to cover at least part of the recess 102 exposed from the spacer 130.

There are no particular restrictions on how the spacer 130 and the upper cover 140 are disposed on the base plate 101, but it is particularly favorable for the base plate 101 and the spacer 130, and the spacer 130 and the upper cover 140 to be bonded to each other. These components may be bonded with a commercially available adhesive, or may be bonded ultrasonically or thermally.

(5) Specific Example of Producing Method

Next, a specific example of methods of producing the biosensor 1 in FIGS. 1 and 2 will be described through reference to FIGS. 11 to 18. FIGS. 11 to 14 and FIGS. 15 to 18 are, respectively, oblique views and cross sections of the biosensor 1 in the various steps of the manufacturing process.

Figure 11:
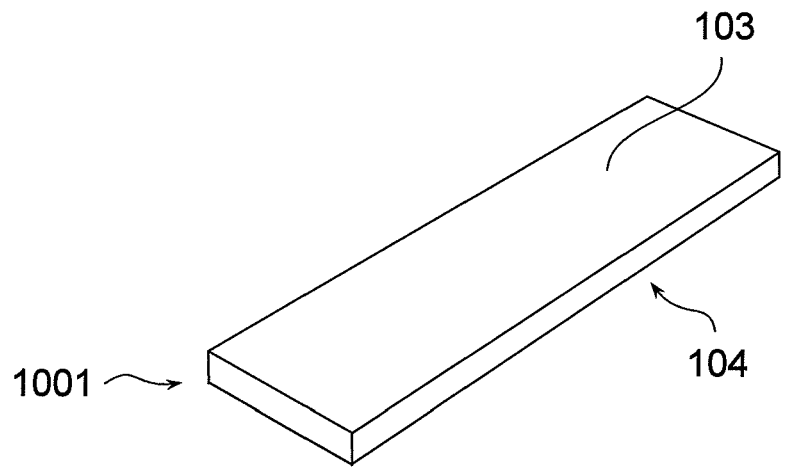
FIG. 11 is an oblique view of an insulating base plate prior to the formation of a recess in the biosensor manufacturing process.
Figure 12:
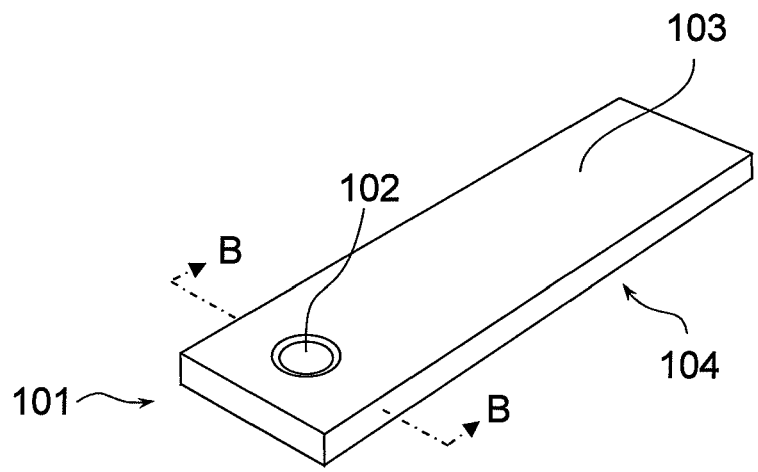
FIG. 12 is an oblique view of the base plate after the formation of a recess in the biosensor manufacturing process.
Figure 15:
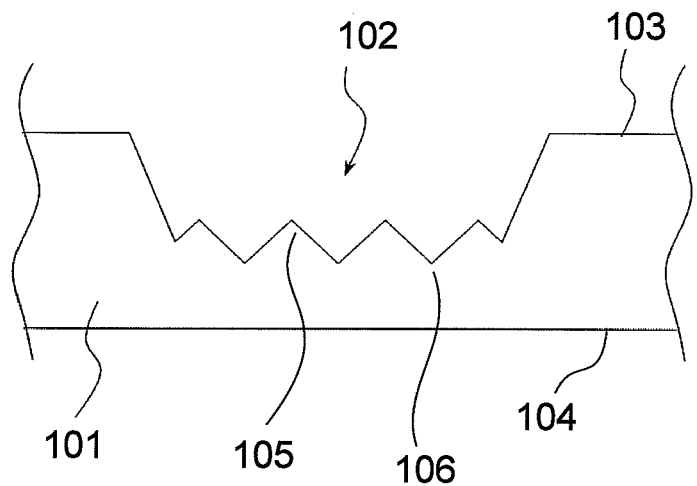
FIG. 15 is a cross section along the B-B line in FIG. 12.

In this example, as shown in FIGS. 11, 12, and 15, the base plate 101 equipped with the recess 102 on the first side 103 is produced by forming the recess 102 by carbon dioxide laser ablation on a flat insulating board 1001. Here, the shape of the lip of the recess 102, the shape of the bottom face, and so on can be suitably varied by means of the pattern of laser irradiation. If the laser is directed at a specific pitch, the material of the base plate will be removed from the portions irradiated with the laser, becoming the valleys 106, and since there is no laser irradiation in between the pitch intervals, these portions become the peaks 105.

Figure 16:
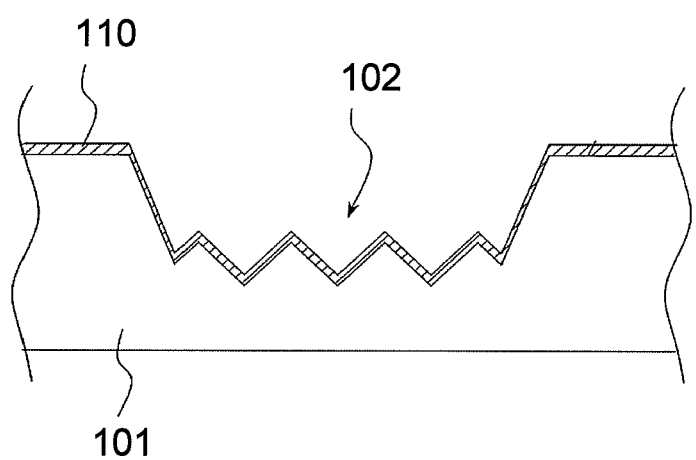
FIG. 16 is a cross section of a base plate in which a conductive layer has been formed.

Next, as shown in FIG. 16, the conductive layer 110 is formed by vapor depositing a conductive material by sputtering over the entire first side 103 of the base plate 101.

Figure 13:
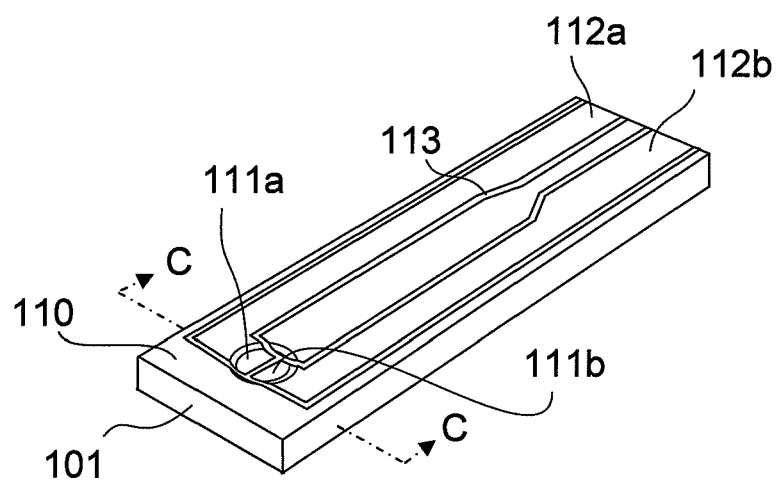
FIG. 13 is an oblique view of the base plate after the formation of the electrode set in the manufacture of the biosensor.
Figure 17:
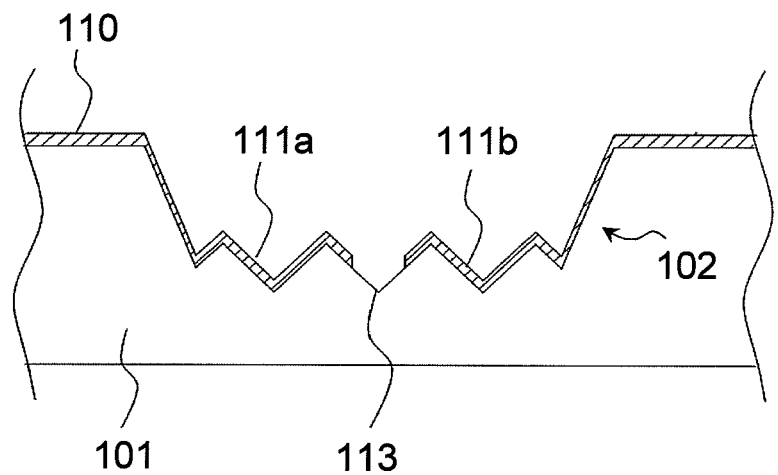
FIG. 17 is a cross section along the C-C line in FIG. 13.

After this, as shown in FIGS. 13 and 17, the surface of the conductive layer 110 is irradiated with a YAG laser, which removes part of the conductive layer 110 and forms the non-conductive tracks 113. Thus forming the non-conductive tracks 113 forms the electrodes 111a and 111b, the terminals 112a and 112b, and the conductive tracks 114a and 114b.

Figure 14:
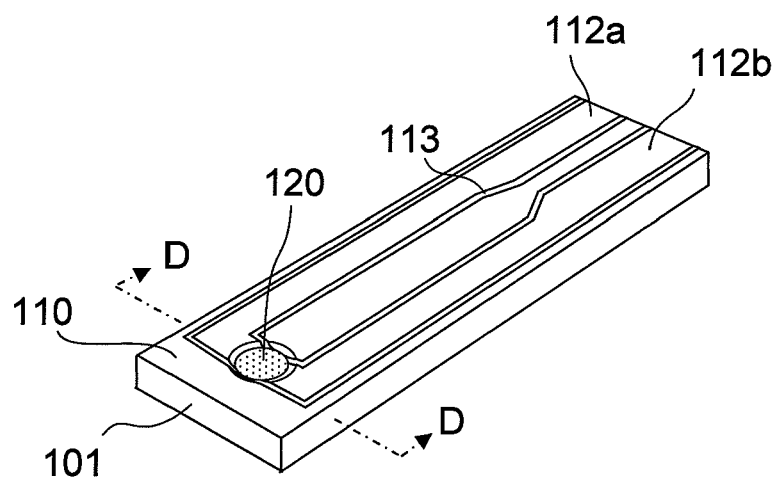
FIG. 14 is an oblique view of the base plate after the reaction layer has been disposed in the manufacture of the biosensor.
Figure 18:
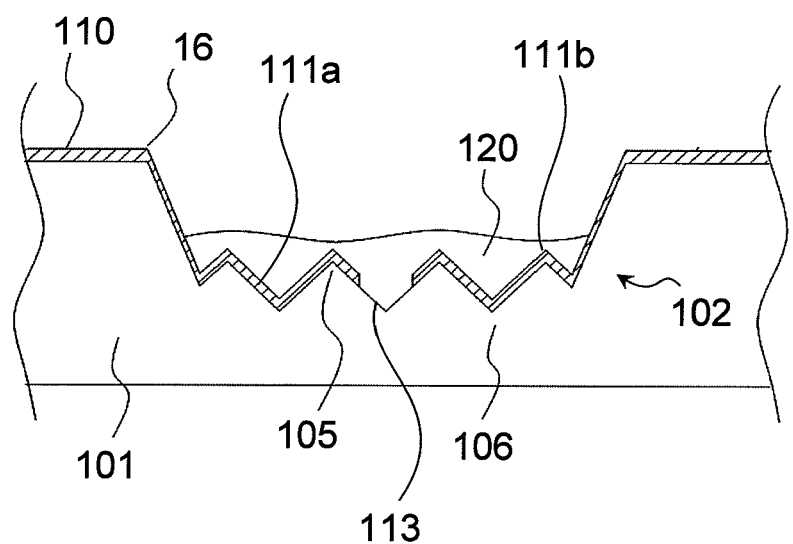
FIG. 18 is a cross section along the D-D line in FIG. 14.

Next, as shown in FIGS. 14 and 18, a liquid containing the reaction reagent is applied so as to cover at least part of the bottom face of the recess 102, and the coating is dried to produce the reagent layer 120.

After this, the biosensor 1 is completed by installing the spacer 130 and the upper cover 140.

C. Detection System

Each of the biosensors discussed in section A. above can be applied to a detection system. For instance, a detection system comprises a detection apparatus to detect the presence of a target substance in a liquid sample from the current value of the biosensor.

Figure 19:
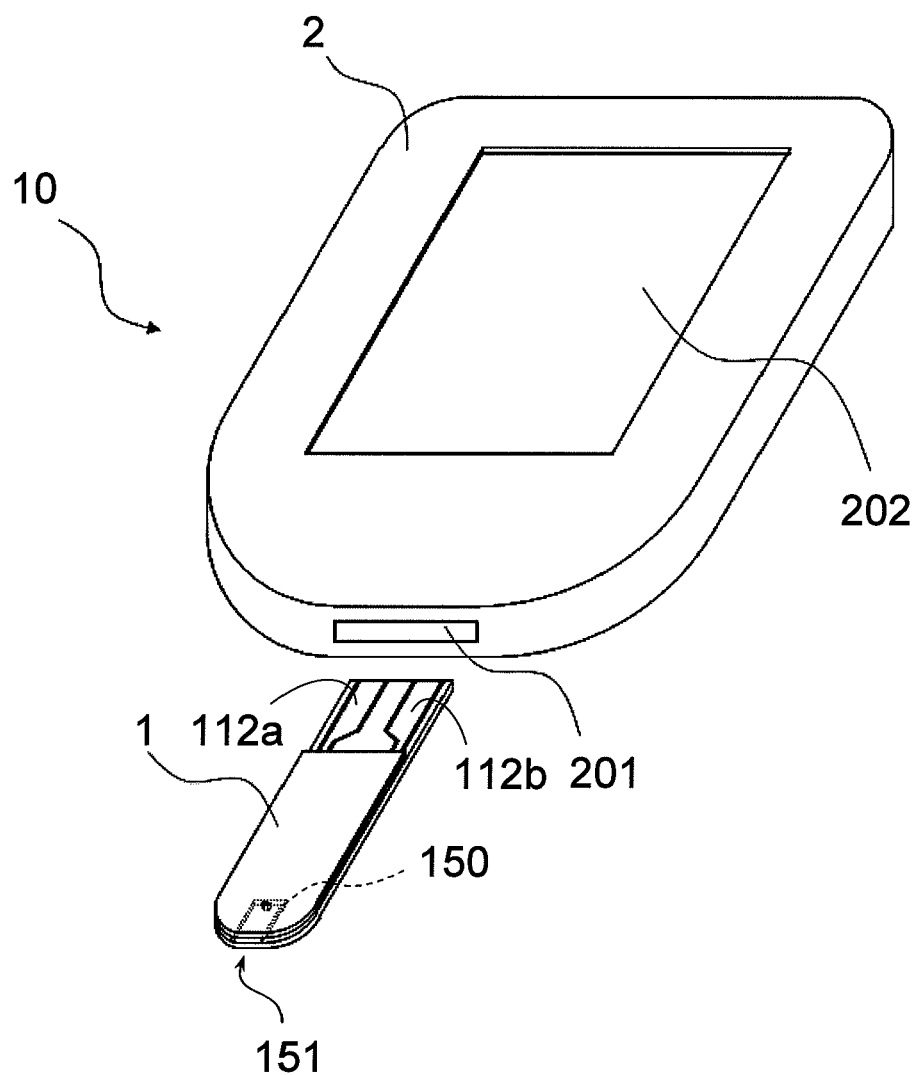
FIG. 19 is an oblique view showing an overview of a measurement system 10.

A measurement system 10 will now be described as an example of a detection system through reference to FIGS. 19 and 20. The measurement system 10 can measure the concentration of a target substance in a liquid sample by two-electrode amperometry. FIG. 19 is an oblique view of what the measurement system 10 looks like, and FIG. 20 is a block diagram showing the main configuration of the measurement system 10.

Overview of Measurement System 10

Figure 20:
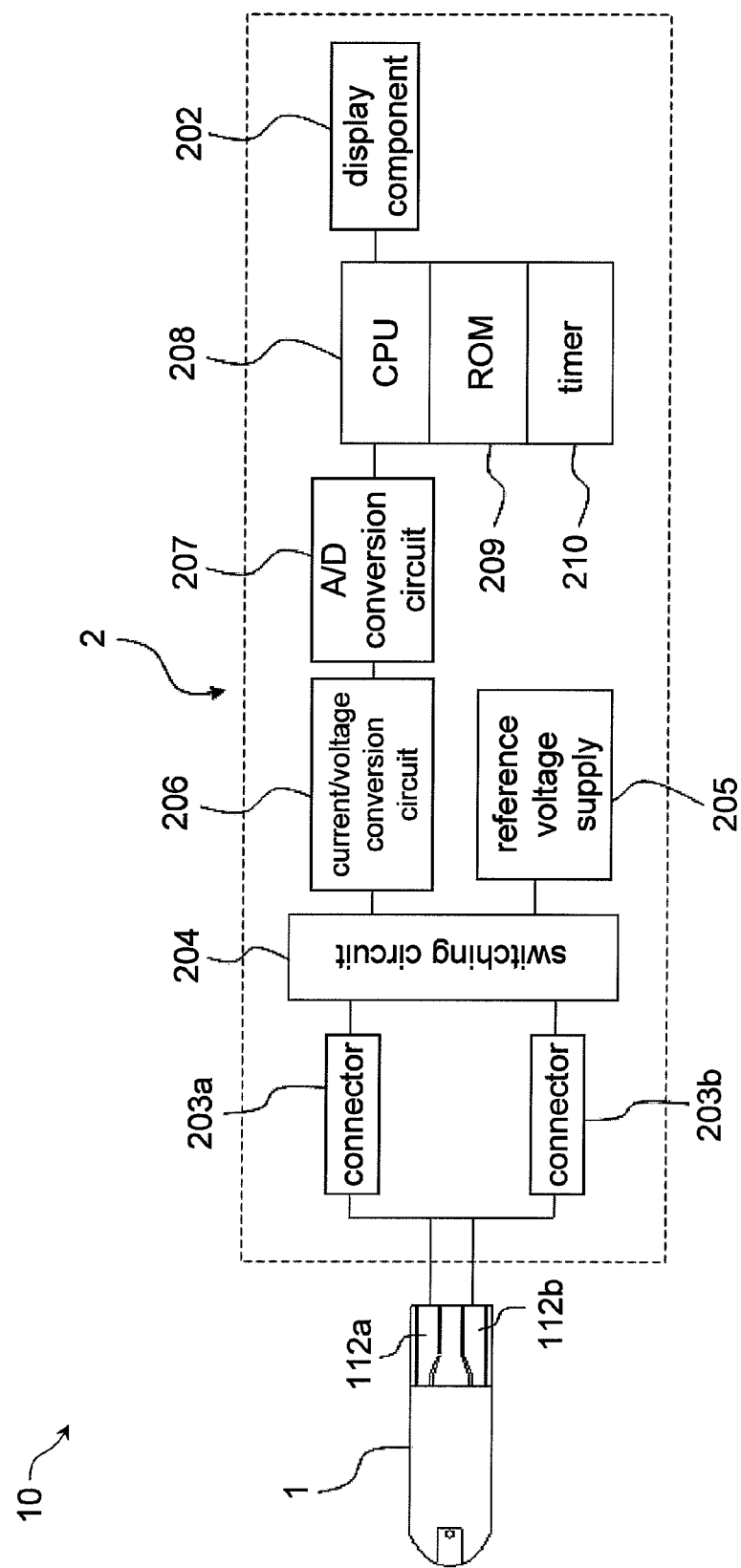
FIG. 20 is a block diagram showing the main configuration of a measurement system 10.

As shown in FIGS. 19 and 20, the measurement system 10 comprises the above-mentioned biosensor 1 and a measurement apparatus 2. The measurement apparatus 2 comprises a mounting component 201 to mount the biosensor, and a display component 202 that has a liquid crystal display panel or the like to provide the user with measurement results and various other information, and further comprises two connectors 203a and 203b, a switching circuit 204, a reference voltage supply 205, an current/voltage conversion circuit 206, an A/D conversion circuit 207, a CPU (central processing unit) 208, a ROM (read-only memory) 209, and a timer 210.

The two connectors 203a and 203b are disposed inside the mounting component 201, and are respectively in contact with the two terminals 112a and 112b of the biosensor 1 mounted in the mounting component 201.

The switching circuit 204 switches between connecting the reference voltage supply 205 to the connectors 203a and 203b, and connecting the current/voltage conversion circuit 206 to the connectors 203a and 203b.

The reference voltage supply 205 applies voltage between the connector 203a and the connector 203b.

The current/voltage conversion circuit 206 accepts current from the biosensor 1 through the connectors 203a and 203b, converts the current into voltage, and outputs it to the A/D conversion circuit 207.

The A/D conversion circuit 207 converts the output value (analog value) from the current/voltage conversion circuit 206 into a pulse (digital value).

The CPU 208 calculates the concentration of a specific component from the pulses from the A/D conversion circuit 207 on the basis of a correction table or a calibration curve stored in the ROM 209. There are no particular restrictions on the means for storing the correction table or calibration curve, and a RAM (random access memory) or other storage medium may be used. The concentration thus calculated is displayed on the display component 202.

The timer 210 keeps track of the time from the start of measurement to the end.

Concentration Measurement with the Measurement System 10

How a concentration is measured with the measurement system 10 will now be described.

When the biosensor 1 is plugged into the mounting component 201, the connectors 203a and 203b come into contact with the terminals 112a and 112b, respectively. When a switch (not shown) inside the mounting component 201 is pressed by the biosensor 1, the CPU 208 determines that the biosensor 1 has been mounted, and the measurement apparatus 2 enters a state of waiting for liquid sample intake. This liquid sample intake standby state is a state in which no liquid sample has yet been subjected to measurement, but the reference voltage supply 205 has started applying voltage to the connectors 203a and 203b under the control of the CPU 208, and the current/voltage conversion circuit 206 has started current measurement.

After this, the user applies a liquid sample to the intake port 151 of the biosensor 1, whereupon capillary action draws the liquid sample through the intake port 151 and into the liquid sample chamber 150.

The liquid sample can, for example, be blood, perspiration, urine, or another liquid sample of biological origin, a liquid sample of environmental origin, a liquid sample of food origin, or the like. For instance, when the biosensor 1 is used as a blood glucose level sensor, the user pricks his own finger, palm, arm, etc., squeezes out a small quantity of blood, and provides this blood as a liquid sample for measurement in the biosensor 1.

The CPU 208 determines from the change in the current value received through the current/voltage conversion circuit 206 that the liquid sample has been drawn into the biosensor 2. Once the intake of a liquid sample has thus been detected, measurement commences. The biosensor 1 may further comprise an electrode used to detect this intake of a liquid sample.

During measurement, the timer 210 keeps track of the measurement time, and the switching circuit 204 switches the circuit at a specific timing on the basis of the time count of the timer 210, thereby converting the current that flowed to the current/voltage conversion circuit 206 into voltage. This voltage is further converted into pulses by the A/D conversion circuit 207. The CPU 208 calculates the concentration of a specific component from these pulses. The value calculated by the CPU 208 is displayed on the display component 202. Other information may also be displayed for the user at the same time.

Upon completion of the measurement, the user can remove the biosensor 1 from the mounting component 201.

The reference voltage supply 205 is designed to impart enough voltage between the two electrodes 111a and 111b to induce the intended electrochemical reaction. This voltage is primarily determined by the chemical reaction and electrodes being used. In general, voltage is applied so that the electrode potential will indicate a voltage higher than the potential rate determiner, so that the electrochemical reaction rate in the active component 107 will be the diffusion rate determiner. As discussed above, though, the liquid sample being measured will sometimes contain various interference substances. Therefore, if a high voltage is applied between the two electrodes and the electrode potential is raised to far, a reaction originating in the interference substances will be induced in addition to the intended reaction, and this will produce electrical signals not originating in the target substance, resulting in erroneous detection. Thus, the voltage applied between the two electrodes is suitably determined according to the presence of interference substances and the intended chemical reaction.

WORKING EXAMPLES

Working examples will now be given to describe the present invention in more specific terms, but the present invention is not limited to or by these examples.

Working Example 1

(1-a) Production of Biosensor

Figure 21:
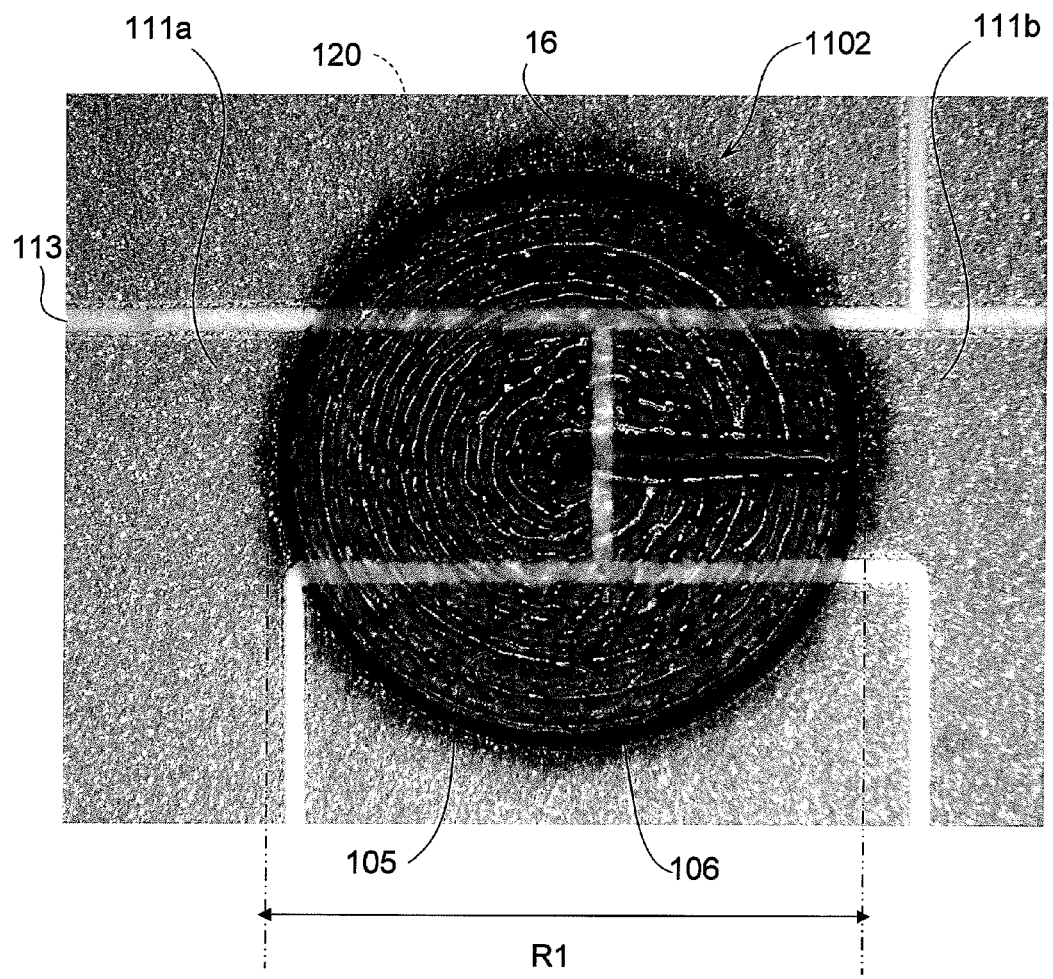
FIG. 21 is a diagram illustrating part of the base plate surface of the biosensor pertaining to Working Example 1.

A biosensor was produced using the method described in section (5) of B. above. FIG. 21 shows a photograph of the surface of the base plate of this biosensor.

More specifically, the base plate 101 was produced by using a flat plate with a thickness of 188 μm and composed of polyethylene terephthalate, which is a non-conductive substance, as an insulating board 1101. More specifically, the insulating board 1101 was irradiated with a laser so as to scribe a plurality of concentric circles, with the radius staggered at 50 μm intervals, so that the maximum diameter would be 2100 μm and the minimum diameter 100 μm, by carbon dioxide laser ablation. This formed a circular recess 1102 as the recess 102.

As shown in FIG. 21, the diameter R1 of the lip 16 of the recess 1102 was 2200 μm, the depth of the deepest part of the valleys 106 was 80 μm, the depth at the apex of the peaks 105 was 20 to 40 μm, and the valleys 106 and peaks 105 repeated at a pitch of 50 μm, forming a repeating pattern. In particular, the valleys 106 and peaks 105 had a shape that scribed concentric circles.

Next, the conductive layer 110 was formed by the vapor deposition of palladium by sputtering. Part of the conductive layer 110 was then removed with a YAG laser to form the non-conductive tracks 113, and to form the electrodes 111a and 111b and the terminals 112a and 112b.

After this, a coating of the reagent layer 120 was applied and dried, and the spacer 130 and the upper cover 140 were provided by bonding, etc., to produce a biosensor. The reagent layer 120 contained glucose dehydrogenase as an enzyme, and hexacyano iron(III) potassium as an electron transfer substance.

(1-b) Measuring Blood Glucose

Figure 22:
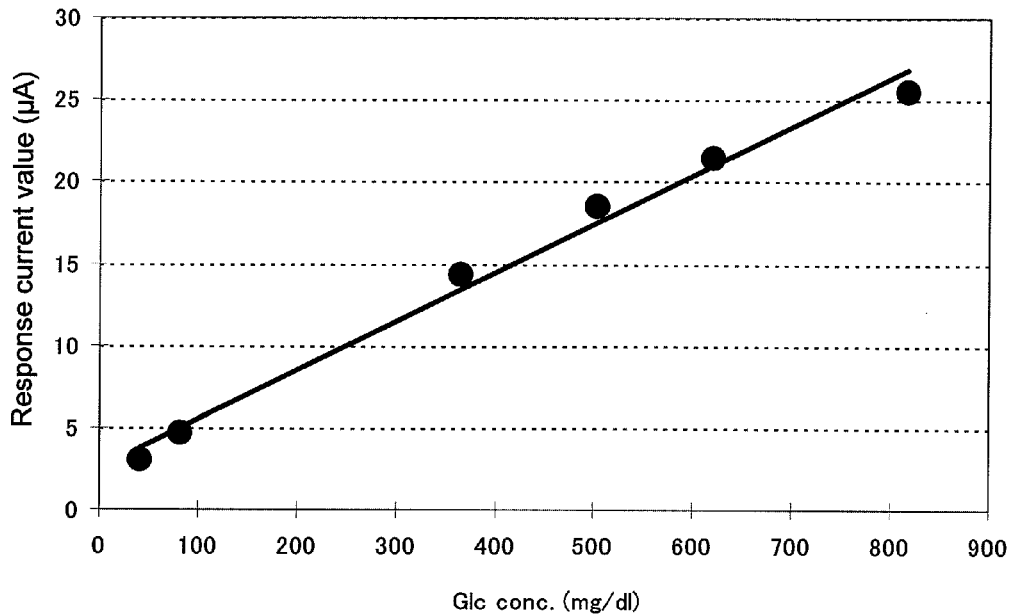
FIG. 22 is a graph of the response current value of the biosensor of Working Example 1 versus glucose concentration.

Using the biosensor produced in (1-a) above, the current value was measured when voltage was applied between the electrodes 111a and 111b. FIG. 22 shows the response current value versus the glucose concentration in the liquid sample. The horizontal axis in FIG. 22 is the glucose concentration, while the vertical axis is the response current value. Blood was used as the liquid sample.

As shown in FIG. 22, the current value obtained by the biosensor of this working example exhibited a good linear relationship with glucose concentration.

(1-c) Checking Reproducibility of Measurement Results

Using the biosensor produced in (1-a) above, measurement was conducted to evaluate reproducibility when the liquid sample intake rate changed. A normal distribution graph (FIG. 23) was produced for the results measured while varying the liquid sample intake rate. The horizontal axis in FIG. 23 is the deviation (%) from the true value, and the vertical axis is the normal cumulative distribution (%).

Figure 23:
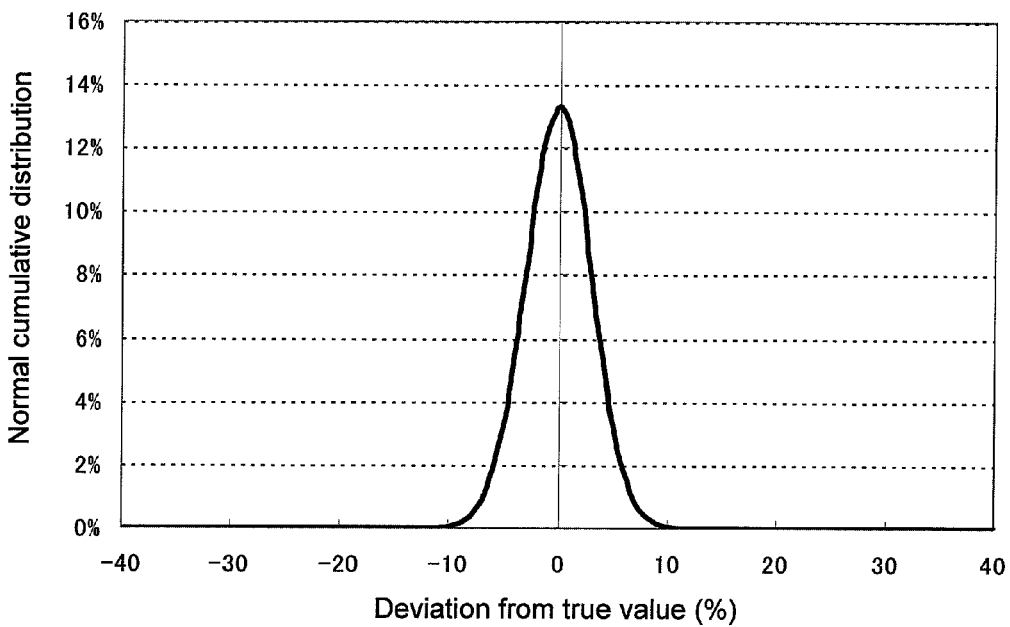
FIG. 23 is a normal distribution graph of when the reproducibility of the biosensor of Working Example 1 was evaluated.

As shown in FIG. 23, with the biosensor in this working example, reproducibility of the measurement results was extremely good, and the liquid sample intake rate that varied with each measurement tended not to produce variance in the measurement result.

The reason for this seems to be that since the electrodes 111a and 111b and the reagent layer 120 are provided inside the recess 1102, the reaction reagent does not readily move during liquid sample intake. In other words, with the biosensor of this working example, even if the liquid sample intake rate varies, the concentration of the reaction reagent inside the recess 1102 tends not to vary, so even though the liquid intake rate changes, the concentration of the target substance can be accurately detected.

Comparative Example 1

Figure 24:
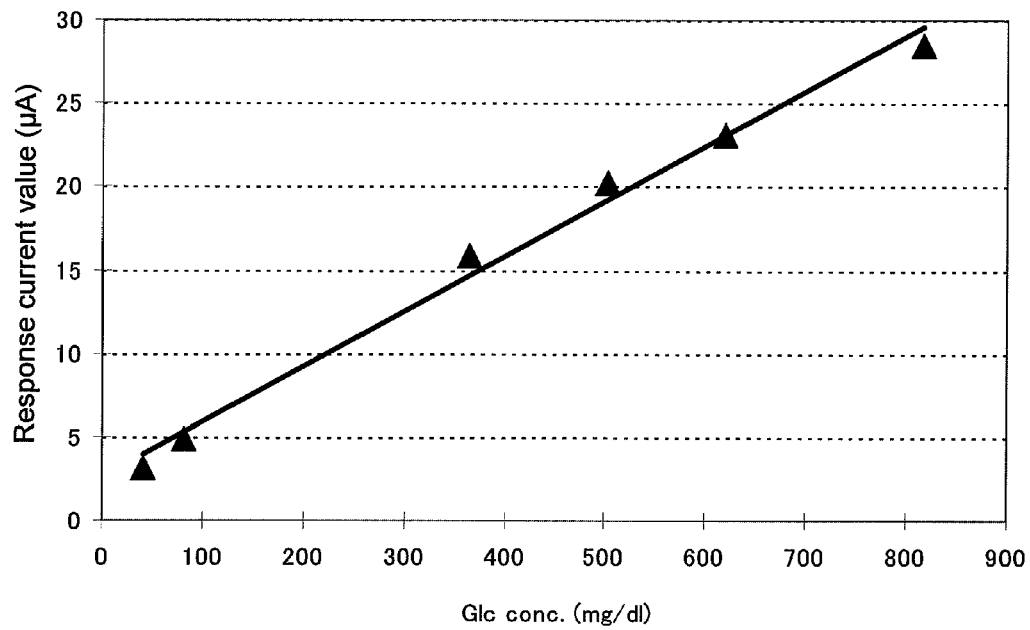
FIG. 24 is a graph of the response current value of the biosensor of a comparative example versus glucose concentration.

The response current value with respect to the glucose concentration was measured in the same manner as in (1-b) above, using a biosensor with the same constitution as the biosensor in Working Example 1, except that it had a flat insulating board with no recess 1102 as the base plate. The measurement results are shown in FIG. 24. The reproducibility of the measurement results was also checked in the same manner as in (1-c) above, the results of which are shown in FIG. 25.

Figure 25:
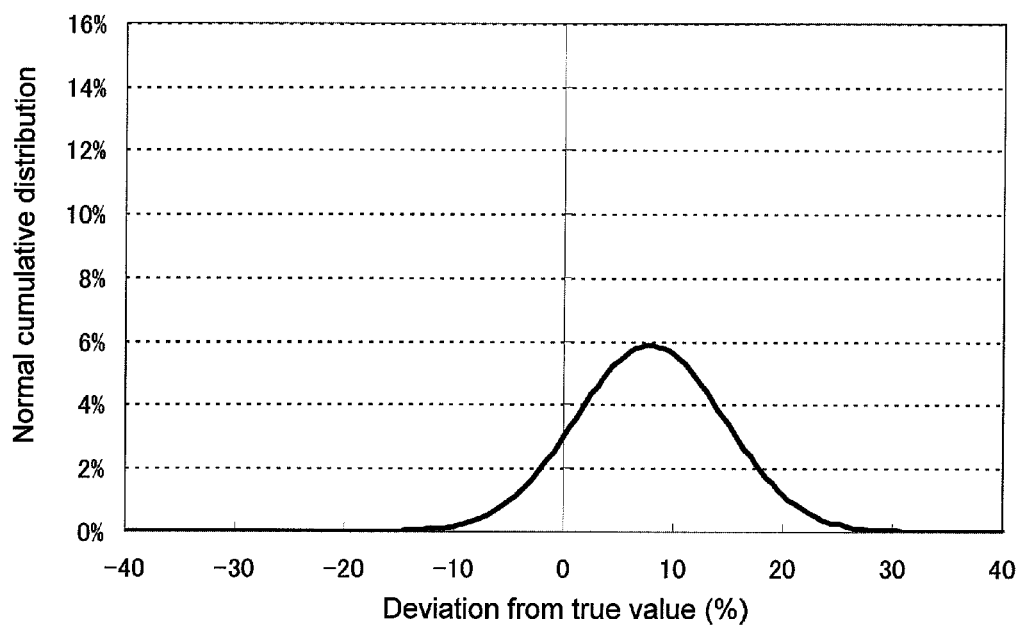
FIG. 25 is a normal distribution graph of when the reproducibility of the biosensor of the comparative example was evaluated.

As shown in FIG. 25, with the biosensor in this comparative example, the measured value deviated greatly from the true value. Also, there was variance in the various measured values, meaning that the reproducibility of the measurement results was much lower than with the biosensor of Working Example 1. The reason the measurement accuracy was so low seems to be that since the biosensor in this comparative example had no recess, the reaction reagent was washed away by the liquid sample, and furthermore, variance in the liquid sample intake rate produced variance in the distribution of the reaction reagent that was washed away.

Working Example 2

Figure 26:
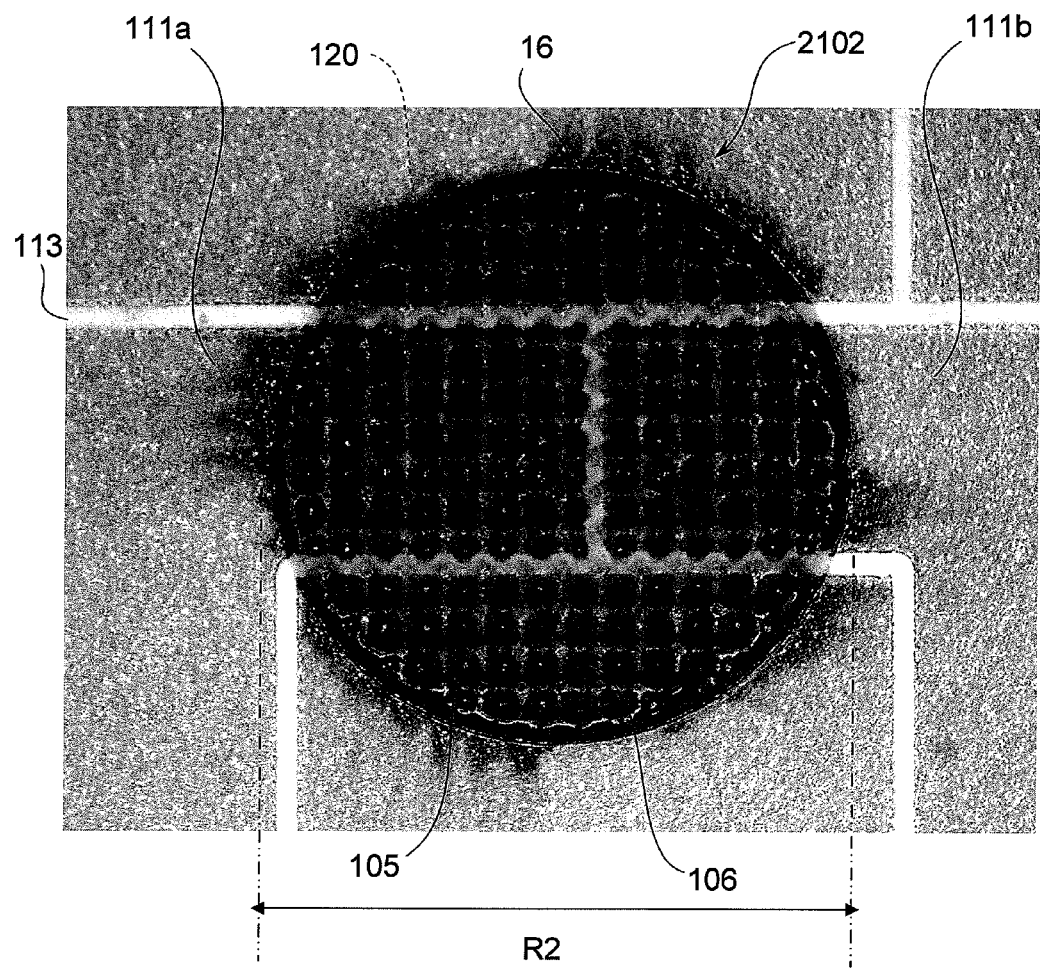
FIG. 26 is a diagram illustrating part of the base plate surface of the biosensor pertaining to Working Example 2.

A biosensor was produced by the same procedure as in Working Example 1, except that a recess 2102 was formed instead of the recess 1102 by irradiating an insulating board with a carbon dioxide laser so as to scribe a circular shape with a diameter of 2100 μm, and irradiating it with a carbon dioxide laser in a grid pattern at a pitch of 150 μm within this circle. FIG. 26 shows a photograph of the upper face of the base plate of this biosensor.

As shown in FIG. 26, the recess 2102 was circular, and the diameter R2 of the lip 16 was 2200 μm. In the recess 2102, the depth of the deepest part of the valleys 106 was 80 μm, and the depth at the apex of the peaks 105 was 20 to 40 μm. The valleys 106 were provided to the entire circular shape of the recess 2102, had a linear shape with a pitch of 140 μm, and the valleys 106 intersected each other in a grid pattern. The portion bounded by the valleys 106 was the peaks 105. The recess 2102 included a repeating pattern of the combination of the peaks 105 and valleys 106

Working Example 3

Figure 27:
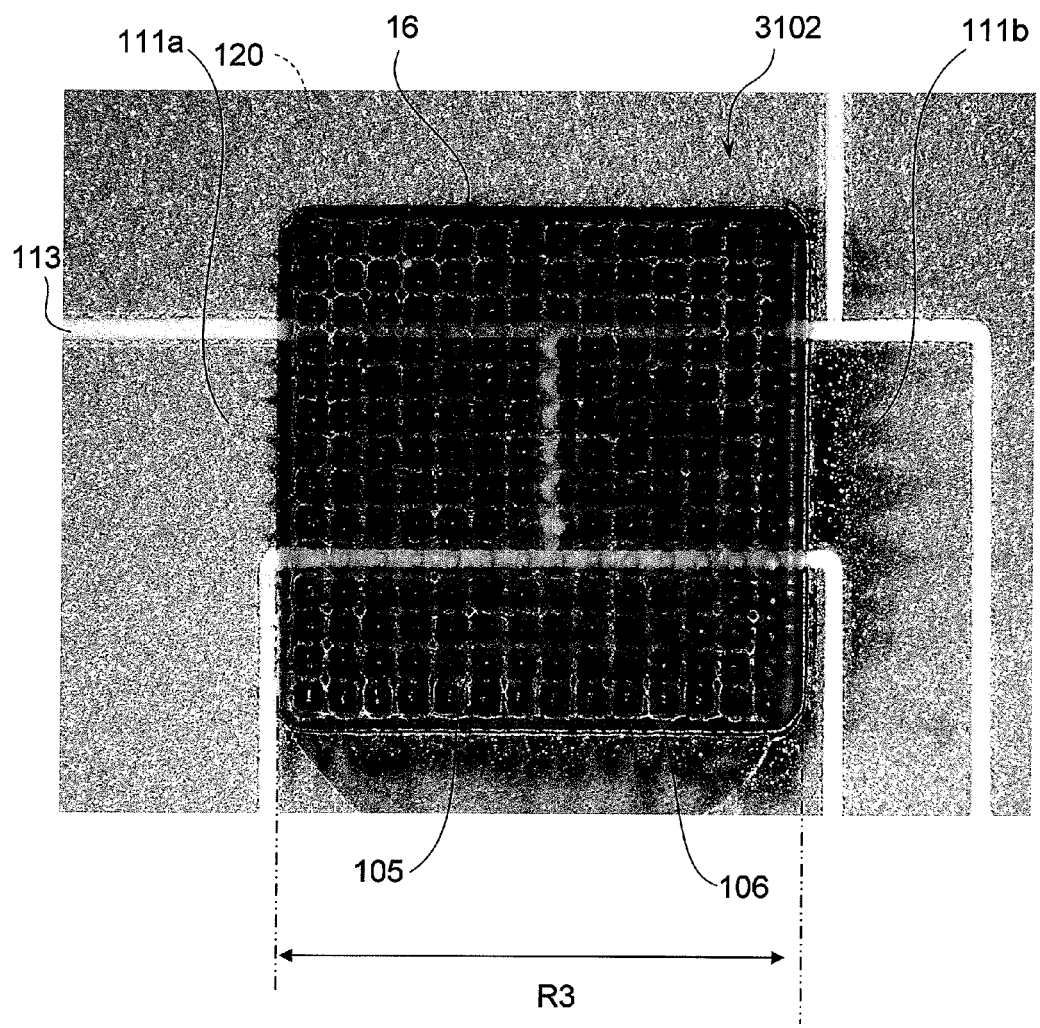
FIG. 27 is a diagram illustrating part of the base plate surface of the biosensor pertaining to Working Example 3.

A biosensor was produced by the same procedure as in Working Example 2, except that a square recess 3102 was formed instead of the circular recess 2102. FIG. 27 shows a photograph of the upper face of the base plate of this biosensor.

More specifically, an insulating board was irradiated with a carbon dioxide laser in a square shape measuring 2100 μm in each of its four sides, and was irradiated with a carbon dioxide laser so as to scribe a grid pattern of straight lines with a length of 2100 μm at a pitch of 150 μm within this square shape.

As shown in FIG. 27, the lip 16 of the recess 3102 was square in shape, with a side length R3 of 2200 μm, and the bottom face structure of the recess 3102 was a grid pattern such that the depth at the deepest part of the valleys 106 was 80 μm, with a pitch of 140 μm. The peaks 105 were the portion bounded by the valleys 106, and the depth at the apex of the peaks 105 was 20 to 40 μm.

The invention claimed is:

1. A biosensor to detect a target substance contained in a liquid sample, comprising:
   an insulating base plate having a first planar side and a second planar side;
   a recess formed in a portion of the insulating base plate that is thinner than a surrounding part of the recess, the recess being depressed in a thickness direction from the first planar side to the second planar side;
   a convex structure formed in a bottom of the recess and having a peak protruding from the second planar side toward the first planar side;
   a working electrode and a counter electrode, at least one of which is disposed along the convex structure; and
   a reaction reagent disposed in the recess so as to be in contact with the at least one of the working electrode and the counter electrode, the reaction reagent reacting with a specific substance in the liquid sample;
   a spacer disposed on the first planar side of the insulating base plate so that at least part of the recess is exposed;
   an upper cover disposed over the spacer to cover the recess exposed from the spacer;
   a liquid sample chamber formed by the insulating base plate including the recess, the spacer, and the upper cover; and
   an intake port disposed above the recess and configured to draw a liquid sample by capillary action from the outside into the liquid sample chamber,
   wherein the liquid sample chamber includes a first space and a second space disposed on the first space so as to communicate with the first space,
   the first space is formed by the recess, and
   the second space is formed by the intake port.

2. The biosensor according to claim 1,
   wherein the recess further includes a concave structure depressed in the thickness direction extending between the first planar side and the second planar side of the insulating base plate.

3. The biosensor according to claim 2,
   wherein the concave structure includes a valley shape that narrows in width toward the second planar side of the insulating base plate.

4. The biosensor according to claim 2,
   wherein the convex structure includes a peak shape that tapers toward a distal end of the peak.

5. The biosensor according to claim 2,
   wherein the shape of the concave structure or the convex structure in a planar direction of the base plate is a dot shape, a linear shape, a square shape, or a curved shape, or is a combination of two or more of these.

6. The biosensor according to claim 2,
   wherein an outer edge of the recess is circular, and
   the concave structure and the convex structure are provided alternately on a bottom face of the recess to scribe a circular shape concentric with the outer edge of the recess.

7. The biosensor according to claim 2,
   wherein an outer edge of the recess is circular, and
   the concave structure is provided in a grid pattern on a bottom face of the recess, and portions surrounded by the concave structure are formed with the convex structures.

8. The biosensor according to claim 2,
   wherein an outer edge of the recess is rectangular, and
   the concave structure is provided in a grid pattern on a bottom face of the recess, and portions surrounded by the concave structure are formed with the convex structures.

9. The biosensor according to claim 1,
   further comprising a liquid sample chamber arranged to hold the liquid sample, above the recess in the thickness direction of the base plate.

10. The biosensor according to claim 1,
    further comprising a vent port arranged to discharge air from an inside of the liquid sample chamber to the outside.

11. The biosensor according to claim 1,
    wherein at least part of a side face of the recess is not perpendicular to the first and second planar sides of the base plate.

12. The biosensor according to claim 1,
    further comprising terminals arranged to electrically connect the working electrode and the counter electrode with a detection device to detect a target substance from a current value of the biosensor.

13. The biosensor according to claim 1,
    wherein the reaction reagent is disposed on the working electrode and the counter electrode.

14. The biosensor according to claim 1,
    wherein the working electrode or the counter electrode contains an electroconductive substance.

15. The biosensor according to claim 14,
    wherein the electroconductive substance includes an inorganic electroconductive substance.

16. The biosensor according to claim 15,
    wherein the working electrode or the counter electrode contains palladium.

17. The biosensor according to claim 14,
    wherein the electroconductive substance includes an organic electroconductive substance.

18. The biosensor according to claim 17,
    wherein the working electrode or the counter electrode contains an electroconductive polymer.

19. The biosensor according to claim 1,
    wherein an enzyme is disposed in the recess.

20. The biosensor according to claim 19,
    wherein oxidase or dehydrogenase is disposed in the recess.

21. The biosensor according to claim 20,
    wherein oxidase or dehydrogenase is disposed in the recess, and
    a substrate of the oxidase and the dehydrogenase is glucose.

22. The biosensor according to claim 1,
    wherein an electron transfer substance is disposed in the recess.

23. The biosensor according to claim 22,
    wherein hexacyano iron (III) potassium is disposed in the recess.

24. The biosensor according to claim 1,
    wherein the reaction reagent is in a dry state.

25. The biosensor according to claim 1,
    wherein the working electrode and the counter electrode are configured to measure a hemocyte component in a liquid sample.

26. The biosensor according to claim 1,
    wherein the working electrode and the counter electrode are configured to measure readily oxidizable substances in a liquid sample.

27. The biosensor according to claim 1,
wherein the electrodes are configured to detect intake of a liquid sample.

28. The biosensor according to claim 1, comprising:
the insulating base plate as a first plate; and
a second plate that is insulating and disposed opposite the first plate,
wherein the reaction reagent and one electrode from among the working electrode and the counter electrode are disposed in the recess on the first plate, and
the other electrode from among the working electrode and the counter electrode is disposed on the second plate.

\* \* \* \* \*